(12) United States Patent
Parker et al.

(10) Patent No.: US 11,633,604 B2
(45) Date of Patent: Apr. 25, 2023

(54) EFFICIENT USE OF AN IMPLANTABLE PULSE GENERATOR BATTERY, AND ASSOCIATED SYSTEMS AND METHODS

(71) Applicant: Nevro Corp., Redwood City, CA (US)

(72) Inventors: Jon Parker, San Jose, CA (US); Bret Foreman, Redwood City, CA (US); Jason Aaron Sutor, Redwood City, CA (US); Sean Knudsen, Redwood City, CA (US)

(73) Assignee: Nevro Corp., Redwood City, CA (US)

( * ) Notice: Subject to any disclaimer, the term of this patent is extended or adjusted under 35 U.S.C. 154(b) by 678 days.

(21) Appl. No.: 16/262,705

(22) Filed: Jan. 30, 2019

(65) Prior Publication Data

US 2019/0232064 A1    Aug. 1, 2019

Related U.S. Application Data

(60) Provisional application No. 62/623,961, filed on Jan. 30, 2018.

(51) Int. Cl.
*A61N 1/36*     (2006.01)
*A61N 1/378*    (2006.01)

(52) U.S. Cl.
CPC ..... *A61N 1/36153* (2013.01); *A61N 1/36062* (2017.08); *A61N 1/36071* (2013.01);
(Continued)

(58) Field of Classification Search
CPC ............ A61N 1/36171; A61N 1/36157; A61N 1/36062; A61N 1/36153
See application file for complete search history.

(56) References Cited

U.S. PATENT DOCUMENTS 3,774,618 A    11/1973   Avery
3,871,382 A     3/1975   Mann
(Continued)

FOREIGN PATENT DOCUMENTS

EP    0754437     1/1997
EP    1610437    12/2005
(Continued)

OTHER PUBLICATIONS

International Search Report and Written Opinion for International Patent Application No. PCT/US2019/015904, dated May 17, 2019, 9 pages.
(Continued)

*Primary Examiner* — Joseph M Dietrich
(74) *Attorney, Agent, or Firm* — Perkins Coie LLP

(57) ABSTRACT

Systems and methods for the efficient use of an implantable pulse generator (IPG) battery are disclosed. A representative system for adjusting an electrical signal of an IPG associated with delivering therapy to a patient comprises a computer readable medium having instructions that cause the IPG to deliver a supply voltage at a first value, adjust the supply voltage from the first value until a threshold break occurs, and, based at least in part of the threshold break, increase the supply voltage from the second value to a third value. As therapy is delivered to the patient, the system iteratively adjusts the supply voltage to approach and reflect a variable minimum voltage needed to provide the requested current to the IPG.

19 Claims, 7 Drawing Sheets

(52) U.S. Cl.
CPC ..... *A61N 1/36139* (2013.01); *A61N 1/36157* (2013.01); *A61N 1/36171* (2013.01); *A61N 1/378* (2013.01)

(56) References Cited

U.S. PATENT DOCUMENTS

| | | |
|---|---|---|
| 4,014,347 A | 3/1977 | Halleck et al. |
| 4,071,032 A | 1/1978 | Schulman |
| 4,082,097 A | 4/1978 | Mann et al. |
| 4,197,850 A | 4/1980 | Schulman et al. |
| 4,230,121 A | 10/1980 | Stanton |
| 4,441,498 A | 4/1984 | Nordling |
| 4,556,063 A | 12/1985 | Thompson |
| 4,632,117 A | 12/1986 | James |
| 4,636,706 A | 1/1987 | Bowman et al. |
| 4,642,479 A | 2/1987 | Lombardi |
| 4,890,616 A | 1/1990 | Pinckaers |
| 5,042,486 A | 8/1991 | Pfeiler et al. |
| 5,052,375 A | 10/1991 | Stark et al. |
| 5,065,083 A | 11/1991 | Owens |
| 5,078,140 A | 1/1992 | Kwoh |
| 5,144,946 A | 9/1992 | Weinberg et al. |
| 5,211,165 A | 5/1993 | Dumoulin et al. |
| 5,257,636 A | 11/1993 | White |
| 5,279,292 A | 1/1994 | Baumann et al. |
| 5,325,873 A | 7/1994 | Hirschi et al. |
| 5,375,596 A | 12/1994 | Twiss et al. |
| 5,425,367 A | 6/1995 | Shapiro et al. |
| 5,591,212 A | 1/1997 | Keimel |
| 5,643,330 A | 7/1997 | Holsheimer et al. |
| 5,727,553 A | 3/1998 | Saad |
| 5,733,313 A | 3/1998 | Barreras, Sr. et al. |
| 5,782,880 A | 7/1998 | Lahtinen et al. |
| 5,807,397 A | 9/1998 | Barreras |
| 5,871,487 A | 2/1999 | Warner et al. |
| 5,893,883 A | 4/1999 | Torgerson |
| 5,916,237 A | 6/1999 | Schu |
| 5,929,615 A | 7/1999 | D'Angelo |
| 5,983,141 A | 11/1999 | Sluijter et al. |
| 6,076,018 A | 6/2000 | Sturman et al. |
| 6,115,634 A | 9/2000 | Donders et al. |
| 6,167,303 A | 12/2000 | Thompson |
| 6,185,452 B1 | 2/2001 | Schulman et al. |
| 6,185,454 B1 | 2/2001 | Thompson |
| 6,192,278 B1 | 2/2001 | Werner et al. |
| 6,198,963 B1 | 3/2001 | Haim et al. |
| 6,223,080 B1 | 4/2001 | Thompson |
| 6,236,888 B1 | 5/2001 | Thompson |
| 6,323,603 B1 | 11/2001 | Persson |
| 6,324,426 B1 | 11/2001 | Thompson |
| 6,387,332 B1 | 5/2002 | Dickinson |
| 6,434,425 B1 | 8/2002 | Thompson |
| 6,438,418 B1 | 8/2002 | Swerdlow et al. |
| 6,440,090 B1 | 8/2002 | Schallhorn |
| 6,453,198 B1 | 9/2002 | Torgerson et al. |
| 6,472,991 B1 | 10/2002 | Schulman et al. |
| 6,474,341 B1 | 11/2002 | Hunter et al. |
| 6,496,729 B2 | 12/2002 | Thompson |
| 6,553,263 B1 | 4/2003 | Meadows et al. |
| 6,650,943 B1 | 11/2003 | Whitehurst et al. |
| 6,712,772 B2 | 3/2004 | Cohen et al. |
| 6,757,561 B2 | 6/2004 | Rubin et al. |
| 6,812,708 B2 | 11/2004 | Bristol |
| 6,862,480 B2 | 3/2005 | Cohen et al. |
| 6,871,090 B1 | 3/2005 | He et al. |
| 6,871,099 B1 | 3/2005 | Whitehurst et al. |
| 6,875,571 B2 | 4/2005 | Crabtree et al. |
| 6,909,915 B2 | 6/2005 | Greatbatch |
| 6,950,707 B2 | 9/2005 | Whitehurst |
| 7,020,523 B1 | 3/2006 | Lu et al. |
| 7,027,860 B2 | 4/2006 | Bruninga et al. |
| 7,054,689 B1 | 5/2006 | Whitehurst et al. |
| 7,082,333 B1 | 7/2006 | Bauhahn et al. |
| 7,120,499 B2 | 10/2006 | Thrope et al. |
| 7,127,288 B2 | 10/2006 | Sturman et al. |
| 7,142,923 B2 | 11/2006 | North et al. |
| 7,167,756 B1 | 1/2007 | Torgerson et al. |
| 7,177,703 B2 | 2/2007 | Boveja et al. |
| 7,180,760 B2 | 2/2007 | Varrichio et al. |
| 7,184,836 B1 | 2/2007 | Meadows et al. |
| 7,206,642 B2 | 4/2007 | Pardo et al. |
| 7,209,792 B1 | 4/2007 | Parramon et al. |
| 7,212,867 B2 | 5/2007 | Van Venrooij et al. |
| 7,236,834 B2 | 6/2007 | Christopherson et al. |
| 7,241,283 B2 | 7/2007 | Putz |
| 7,244,150 B1 | 7/2007 | Brase et al. |
| 7,254,449 B2 | 8/2007 | Karunasiri |
| 7,266,412 B2 | 9/2007 | Stypulkowski |
| 7,313,440 B2 | 12/2007 | Miesel |
| 7,329,262 B2 | 2/2008 | Gill |
| 7,337,010 B2 | 2/2008 | Howard et al. |
| 7,381,441 B2 | 6/2008 | Leung et al. |
| 7,425,142 B1 | 9/2008 | Putz |
| 7,437,193 B2 | 10/2008 | Parramon et al. |
| 7,489,968 B1 | 2/2009 | Alexander et al. |
| 7,571,002 B2 | 8/2009 | Thrope et al. |
| 7,606,622 B2 | 10/2009 | Reeve |
| 7,616,990 B2 | 11/2009 | Chavan et al. |
| 7,636,602 B2 | 12/2009 | Baru Fassio et al. |
| 7,641,992 B2 | 1/2010 | Howard et al. |
| 7,650,191 B1 | 1/2010 | Lim et al. |
| 7,682,745 B2 | 3/2010 | Howard et al. |
| 7,697,984 B2 | 4/2010 | Hill et al. |
| 7,702,379 B2 | 4/2010 | Avinash et al. |
| 7,769,462 B2 | 8/2010 | Meadows et al. |
| 7,801,601 B2 | 9/2010 | Maschino et al. |
| 7,801,615 B2 | 9/2010 | Meadows et al. |
| 7,805,189 B2 | 9/2010 | Stein et al. |
| 7,818,068 B2 | 10/2010 | Meadows et al. |
| 7,826,901 B2 | 11/2010 | Lee et al. |
| 7,848,812 B2 | 12/2010 | Crowley et al. |
| 7,856,277 B1 | 12/2010 | Thacker et al. |
| 7,865,245 B2 | 1/2011 | Torgerson et al. |
| 7,879,495 B2 | 2/2011 | Howard et al. |
| 7,894,905 B2 | 2/2011 | Pless et al. |
| 7,941,220 B2 | 5/2011 | Tobacman |
| 7,957,797 B2 | 6/2011 | Bourget et al. |
| 7,957,809 B2 | 6/2011 | Bourget et al. |
| 7,996,055 B2 | 8/2011 | Hauck et al. |
| 8,016,776 B2 | 9/2011 | Bourget et al. |
| 8,128,600 B2 | 3/2012 | Gill |
| 8,131,357 B2 | 3/2012 | Bradley et al. |
| 8,150,521 B2 | 4/2012 | Crowley et al. |
| 8,170,675 B2 | 5/2012 | Alataris et al. |
| 8,190,259 B1 | 5/2012 | Smith et al. |
| 8,197,494 B2 | 6/2012 | Jaggi et al. |
| 8,209,021 B2 | 6/2012 | Alataris et al. |
| 8,209,028 B2 | 6/2012 | Skelton et al. |
| 8,224,453 B2 | 7/2012 | De Ridder |
| 8,355,791 B2 | 1/2013 | Moffitt |
| 8,355,797 B2 | 1/2013 | Caparso et al. |
| 8,380,318 B2 | 2/2013 | Kishawi et al. |
| 8,423,147 B2 | 4/2013 | Alataris et al. |
| 8,428,748 B2 | 4/2013 | Alataris et al. |
| 8,571,679 B2 | 10/2013 | Parramon et al. |
| 8,583,954 B2 | 11/2013 | Dinsmoor |
| 8,712,534 B2 | 4/2014 | Wei |
| 8,929,986 B2 | 1/2015 | Parker |
| 8,965,514 B2 | 2/2015 | Bikson et al. |
| 9,061,152 B2 | 6/2015 | Shi et al. |
| 9,192,769 B2 | 11/2015 | Donofrio et al. |
| 9,227,076 B2 | 1/2016 | Sharma et al. |
| 9,409,020 B2 | 8/2016 | Parker et al. |
| 9,466,997 B2 | 10/2016 | Silva |
| 9,533,164 B2 | 1/2017 | Erickson |
| 9,764,147 B2 | 9/2017 | Togerson |
| 10,173,062 B2 | 1/2019 | Parker |
| 11,058,875 B1 | 7/2021 | Zinner |
| 2002/0068956 A1 | 6/2002 | Bloemer et al. |
| 2002/0107554 A1 | 8/2002 | Biggs et al. |
| 2002/0193844 A1 | 12/2002 | Michelson et al. |
| 2003/0107349 A1 | 6/2003 | Haydock et al. |
| 2003/0110058 A1 | 6/2003 | Adie |
| 2003/0114899 A1 | 6/2003 | Woods et al. |

(56) References Cited

U.S. PATENT DOCUMENTS

| | | |
|---|---|---|
| 2003/0135241 A1 | 7/2003 | Leonard et al. |
| 2003/0191504 A1 | 10/2003 | Meadows et al. |
| 2003/0195581 A1 | 10/2003 | Meadows et al. |
| 2003/0199952 A1 | 10/2003 | Stolz et al. |
| 2003/0204221 A1 | 10/2003 | Rodriguez et al. |
| 2003/0204222 A1 | 10/2003 | Leinders et al. |
| 2003/0208244 A1 | 11/2003 | Stein et al. |
| 2004/0034393 A1 | 2/2004 | Hansen et al. |
| 2004/0098060 A1 | 5/2004 | Ternes |
| 2004/0176812 A1 | 9/2004 | Knudson et al. |
| 2004/0186544 A1 | 9/2004 | King |
| 2004/0199214 A1 | 10/2004 | Merfeld et al. |
| 2004/0210290 A1 | 10/2004 | Omar-Pasha |
| 2004/0215287 A1 | 10/2004 | Swoyer et al. |
| 2004/0225333 A1 | 11/2004 | Greatbatch |
| 2005/0004417 A1 | 1/2005 | Nelson et al. |
| 2005/0004638 A1 | 1/2005 | Cross |
| 2005/0025480 A1 | 2/2005 | Yeh |
| 2005/0038489 A1 | 2/2005 | Grill |
| 2005/0049664 A1 | 3/2005 | Harris et al. |
| 2005/0075695 A1 | 4/2005 | Schommer et al. |
| 2005/0131483 A1 | 6/2005 | Zhao |
| 2005/0143787 A1 | 6/2005 | Boveja et al. |
| 2005/0174098 A1 | 8/2005 | Watanabe |
| 2005/0178372 A1 | 8/2005 | Kesler et al. |
| 2005/0203583 A1 | 9/2005 | Twetan et al. |
| 2005/0203584 A1 | 9/2005 | Twetan et al. |
| 2005/0218726 A1 | 10/2005 | Jenson |
| 2005/0266301 A1 | 12/2005 | Smith et al. |
| 2005/0267546 A1 | 12/2005 | Parramon et al. |
| 2006/0004422 A1 | 1/2006 | De Ridder |
| 2006/0089697 A1 | 4/2006 | Cross et al. |
| 2006/0122655 A1 | 6/2006 | Greatbatch et al. |
| 2006/0190060 A1 | 8/2006 | Greeninger |
| 2006/0224208 A1 | 10/2006 | Naviaux |
| 2007/0060955 A1 | 3/2007 | Strother et al. |
| 2007/0060968 A1 | 3/2007 | Strother et al. |
| 2007/0060980 A1 | 3/2007 | Strother et al. |
| 2007/0066995 A1 | 3/2007 | Strother et al. |
| 2007/0093875 A1 | 4/2007 | Chavan et al. |
| 2007/0111587 A1 | 5/2007 | Ries et al. |
| 2007/0129768 A1 | 6/2007 | He |
| 2007/0142728 A1 | 6/2007 | Penner |
| 2007/0142874 A1 | 6/2007 | John |
| 2007/0162088 A1 | 7/2007 | Chen et al. |
| 2007/0265489 A1 | 11/2007 | Fowler et al. |
| 2007/0270916 A1 | 11/2007 | Fischell et al. |
| 2008/0015644 A1 | 1/2008 | Julian |
| 2008/0039904 A1 | 2/2008 | Bulkes et al. |
| 2008/0058901 A1 | 3/2008 | Ternes et al. |
| 2008/0065182 A1 | 3/2008 | Strother et al. |
| 2008/0077184 A1 | 3/2008 | Denker et al. |
| 2008/0097554 A1 | 4/2008 | Payne et al. |
| 2008/0125833 A1 | 5/2008 | Bradley et al. |
| 2008/0129225 A1 | 6/2008 | Yamamoto et al. |
| 2008/0132926 A1 | 6/2008 | Eichmann et al. |
| 2008/0140153 A1 | 6/2008 | Burdulis |
| 2008/0156333 A1 | 7/2008 | Galpern et al. |
| 2008/0216846 A1 | 9/2008 | Levin |
| 2008/0243210 A1 | 10/2008 | Doron |
| 2008/0255631 A1 | 10/2008 | Sjostedt et al. |
| 2008/0262563 A1 | 10/2008 | Sjostedt |
| 2008/0294219 A1 | 11/2008 | Osypka et al. |
| 2008/0319441 A1 | 12/2008 | Seid |
| 2009/0012576 A1 | 1/2009 | Erbstoeszer et al. |
| 2009/0017700 A1 | 1/2009 | Zart et al. |
| 2009/0018600 A1 | 1/2009 | Deininger et al. |
| 2009/0018607 A1 | 1/2009 | Crowley et al. |
| 2009/0048643 A1* | 2/2009 | Erickson ............... A61N 1/378 607/59 |
| 2009/0132010 A1 | 5/2009 | Kronberg |
| 2009/0157138 A1 | 6/2009 | Errico et al. |
| 2009/0157142 A1 | 6/2009 | Cauller |
| 2009/0204119 A1 | 8/2009 | Bleich et al. |
| 2009/0204173 A1 | 8/2009 | Fang |
| 2009/0210029 A1 | 8/2009 | Tsui |
| 2009/0228074 A1 | 9/2009 | Edgell et al. |
| 2009/0248094 A1 | 10/2009 | McDonald |
| 2009/0248118 A1 | 10/2009 | Bradley et al. |
| 2009/0270948 A1 | 10/2009 | Nghiem et al. |
| 2009/0281596 A1 | 11/2009 | King |
| 2009/0281599 A1 | 11/2009 | Thacker et al. |
| 2009/0287946 A1 | 11/2009 | Lin |
| 2010/0004654 A1 | 1/2010 | Schmitz et al. |
| 2010/0010567 A1 | 1/2010 | Deem et al. |
| 2010/0038132 A1 | 2/2010 | Kinney et al. |
| 2010/0049275 A1 | 2/2010 | Chavan et al. |
| 2010/0094115 A1 | 4/2010 | Pond, Jr. et al. |
| 2010/0094231 A1 | 4/2010 | Bleich et al. |
| 2010/0106223 A1 | 4/2010 | Grevious et al. |
| 2010/0137943 A1 | 6/2010 | Zhu |
| 2010/0137944 A1 | 6/2010 | Zhu |
| 2010/0144281 A1 | 6/2010 | Kim et al. |
| 2010/0144283 A1 | 6/2010 | Curcio et al. |
| 2010/0168818 A1 | 7/2010 | Barror et al. |
| 2010/0233896 A1 | 9/2010 | Dilmaghanian |
| 2010/0274312 A1 | 10/2010 | Alataris et al. |
| 2010/0274314 A1 | 10/2010 | Alataris et al. |
| 2010/0274317 A1 | 10/2010 | Parker et al. |
| 2010/0305631 A1 | 12/2010 | Bradley et al. |
| 2010/0305663 A1 | 12/2010 | Aghassian |
| 2010/0324570 A1 | 12/2010 | Rooney et al. |
| 2010/0331920 A1 | 12/2010 | DiGiore et al. |
| 2011/0054583 A1 | 3/2011 | Litt et al. |
| 2011/0060282 A1 | 3/2011 | Dogwiler et al. |
| 2011/0112601 A1 | 5/2011 | Meadows et al. |
| 2011/0112609 A1 | 5/2011 | Peterson |
| 2011/0112610 A1 | 5/2011 | Rahman et al. |
| 2011/0118661 A1 | 5/2011 | Pless et al. |
| 2011/0144468 A1 | 6/2011 | Boggs et al. |
| 2011/0160804 A1 | 6/2011 | Penner |
| 2011/0184488 A1 | 7/2011 | De Ridder |
| 2011/0224710 A1 | 9/2011 | Bleich |
| 2011/0245708 A1 | 10/2011 | Finkel et al. |
| 2011/0270363 A1 | 11/2011 | Schramm |
| 2011/0301679 A1 | 12/2011 | Rezai |
| 2012/0066534 A1 | 3/2012 | Dinsmoor |
| 2012/0095744 A1 | 4/2012 | Rahman et al. |
| 2012/0101551 A1 | 4/2012 | Aghassian et al. |
| 2012/0239108 A1 | 9/2012 | Foutz et al. |
| 2012/0253440 A1 | 10/2012 | Grohmann |
| 2012/0315798 A1 | 12/2012 | Poon et al. |
| 2013/0035740 A1 | 2/2013 | Sharma et al. |
| 2013/0066399 A1 | 3/2013 | Min |
| 2013/0066411 A1 | 3/2013 | Thacker et al. |
| 2013/0238048 A1 | 9/2013 | Almendinger et al. |
| 2013/0282078 A1 | 10/2013 | Wacnik |
| 2014/0180361 A1 | 1/2014 | Burdick et al. |
| 2014/0067016 A1 | 3/2014 | Kaula |
| 2014/0081350 A1 | 3/2014 | Zhu |
| 2014/0121787 A1 | 5/2014 | Yamazaki |
| 2014/0217291 A1 | 8/2014 | Deutscher |
| 2014/0277268 A1 | 9/2014 | Lee |
| 2014/0343622 A1 | 11/2014 | Alataris |
| 2015/0005842 A1 | 1/2015 | Lee |
| 2015/0039047 A1 | 2/2015 | Parker |
| 2015/0039048 A1 | 2/2015 | Woods |
| 2015/0088227 A1 | 3/2015 | Shishilla et al. |
| 2015/0151125 A1 | 6/2015 | Zhu |
| 2015/0165209 A1 | 6/2015 | Grandhe |
| 2015/0321000 A1 | 11/2015 | Rosenbluth |
| 2016/0114171 A1 | 4/2016 | Parker |
| 2016/0124455 A1 | 5/2016 | Sambucco et al. |
| 2016/0158551 A1 | 6/2016 | Kent et al. |
| 2016/0256696 A1 | 9/2016 | Sharma et al. |
| 2016/0271392 A1 | 9/2016 | Vallejo et al. |
| 2017/0189686 A1 | 7/2017 | Steinke et al. |
| 2017/0197079 A1 | 7/2017 | Illegems |
| 2017/0202607 A1 | 7/2017 | Shelton |
| 2018/0345022 A1 | 12/2018 | Steinke et al. |
| 2019/0022382 A1 | 1/2019 | Gerasimenko et al. |
| 2019/0232064 A1 | 8/2019 | Parker |

(56) References Cited

U.S. PATENT DOCUMENTS

| | | |
|---|---|---|
| 2019/0341803 A1 | 11/2019 | Cook |
| 2021/0335285 A1 | 10/2021 | Liu |

FOREIGN PATENT DOCUMENTS

| | | |
|---|---|---|
| EP | 2243510 | 10/2010 |
| JP | 2002090196 | 3/2002 |
| WO | WO-20080121110 | 10/2008 |
| WO | WO-2011094074 A1 | 8/2011 |
| WO | WO-2012054234 | 4/2012 |

OTHER PUBLICATIONS

North et al., "Spinal Cord Stimulation for Axial Low Back Pain," Spine, vol. 30, No. 12, 2005, 7 pages.

North et al., "Spinal Cord Stimulation for Chronic, Intractable Pain: Experience over Two Decades," Neurosurgery, vol. 32, No. 2, Mar. 1993, 12 pages.

Kumar et al., "Spinal Cord Stimulation in Treatment of Chronic Benign Pain: Challenges in Treatment Planning and Present Status, a 22-Year Experience," Neurosurgery, vol. 58, No. 3, Mar. 2006, 16 pages.

Extended European Search Report for European Patent Application No. 19748155.9, Applicant: Nevro Corp., dated Sep. 21, 2021, 7 pages.

Gainer et al., "Use of the Peripheral Nerve Stimulator and Standard, Unsheathed Needles in Performing Regional Nerve Blocks," CRNA: The Clinical Forum for Nurse Anesthetists, vol. 3, No. 4, Nov. 1992, 4 pages.

Holst et al., "Nervous Control of Pancreatic exocrine secretion in pigs," Acta, Physiol. Scan 1979, 105, 19 pages.

Huxely et al., "Excitation and Conduction in Nerve: Quantitative Analysis," Science, Sep. 11, 1964; 145: 1154-9.

Klein, "Continuous Peripheral Nerve Blocks," Anesthesiology, vol. 103, No. 5, Nov. 2005, 3 pages.

Linderoth et al., "Mechanisms of Spinal Cord Stimulation in Painful Syndromes: Role of Animal Models," Pain Medicine, vol. 7, No. S1, 2006, 13 pages.

Mediati, R.D., , "Mechanisms of Spinal Cord Stimulation," Florence, Oct. 2, 2002, 31 pages.

Paterson CA et al., "Determinants of Occurrence and Volume of Transpyloric Flow During Gastric Emptying of Liquids in Dogs: Importance of Vagal Input," Dig Dis Sci, 2000, 45: 1509-1516.

Vadalouca et al., "Therapeutic Management of Chronic Neuropathic Pain: An Examination of Pharmacologic Treatment," Annals New York Academy of Sciences, 2006, pp. 164-186.

\* cited by examiner

EFFICIENT USE OF AN IMPLANTABLE PULSE GENERATOR BATTERY, AND ASSOCIATED SYSTEMS AND METHODS

CROSS-REFERENCE TO RELATED APPLICATION

The present application claims priority to U.S. Provisional Application 62/623,961, filed on Jan. 30, 2018 and incorporated herein by reference in its entirety.

TECHNICAL FIELD

The present technology is directed generally to the efficient use of an implantable pulse generator battery. Some embodiments include using battery circuitry to make battery usage by the implantable pulse generator more efficient and thereby extend the life of the battery.

BACKGROUND

Neurological stimulators have been developed to treat pain, movement disorders, functional disorders, spasticity, cancer, cardiac disorders, and various other medical conditions. Implantable neurological stimulation systems generally have an implantable signal generator and one or more leads that deliver electrical pulses to neurological tissue or muscle tissue. For example, several neurological stimulation systems for spinal cord stimulation (SCS) have cylindrical leads that include a lead body with a circular cross-sectional shape and one or more conductive rings (e.g., contacts) spaced apart from each other at the distal end of the lead body. The conductive rings operate as individual electrodes and, in many cases, the SCS leads are implanted percutaneously through a needle inserted into the epidural space, with or without the assistance of a stylet.

Once implanted, the signal generator applies electrical pulses to the electrodes, which in turn modify the function of the patient's nervous system, such as by altering the patient's responsiveness to sensory stimuli and/or altering the patient's motor-circuit output. In SCS therapy for the treatment of pain, the signal generator applies electrical pulses to the spinal cord via the electrodes. In conventional SCS therapy, electrical pulses are used to generate sensations (known as paresthesia) that mask or otherwise alter the patient's sensation of pain. For example, in many cases, patients report paresthesia as a tingling sensation that is perceived as less uncomfortable than the underlying pain sensation.

In contrast to traditional or conventional (i.e., paresthesia-based) SCS, a form of paresthesia-free SCS has been developed that uses therapy signal parameters that treat the patient's sensation of pain without generating paresthesia or otherwise using paresthesia to mask the patient's sensation of pain. One of several advantages of paresthesia-free SCS therapy systems is that they eliminate the need for uncomfortable paresthesia, which many patients find objectionable. However, a challenge with paresthesia-free SCS therapy systems is that the signal may be delivered at frequencies, amplitudes, and/or pulse widths that use more power than conventional SCS systems. As a result, the battery of the implanted system can discharge and become depleted at an accelerated rate, thereby making battery life an important design concern.

An additional follow-on challenge with providing non-paresthesia-generating SCS via an implanted pulse generator is that, in at least some cases, it may be difficult to maintain an effective signal as the charge available from the pulse generator battery decreases. One approach to power consumption challenges in the context of conventional SCS systems is to increase the frequency with which the pulse generator is charged, but this can be inconvenient for the patient. Another approach is to add signal conditioning hardware, for example, to boost the voltage provided by the battery as the battery discharges. A drawback with this approach is that it can be inefficient.

Yet another follow-on challenge with providing non-paresthesia-generating SCS via an implanted pulse generator is that, in at least some cases, overcharging or over-discharging the battery beyond a particular threshold can cause irreversible damage to the battery and its components. For example, over-discharging the battery below a particular threshold can cause "thermal runaway," wherein battery charge conditions (e.g., high voltages) can lead to self-sustaining increases in temperature, thereby causing battery components (e.g., the negative electrode or electrolyte) to breakdown. If a battery does go beyond the particular threshold, the battery may become unusable and need to be explanted. One approach to overcharging or over-discharging challenges is to avoid passing the particular thresholds beyond which "thermal runaway" occurs by decreasing the charge rate of the battery as the threshold limits are approached. This is often referred to as "trickle charging," which corresponds to a charge rate less than the typical charge rate used during normal operation. For example, trickle charging may switch the typical charge rate to the trickle charge rate at a voltage threshold below an upper damage threshold (UDT) to ensure the UDT is not breached. If the typical charge rate for a battery is C/2 (i.e., one-half of the battery capacity), the trickle charge rate can be, for example, C/5, C/10, C/25, etc. One drawback of this approach is that it can be inefficient, as it can take longer to charge the battery to a full capacity at a reduced charge rate. Another drawback of this approach is that it can cause delay and frustration for a patient who may be waiting for the battery to reach a fully-charged state.

Accordingly, there remains a need for effective and efficient therapy signal delivery, despite the possibility of increased power consumption resulting from the signal delivery parameters used for paresthesia-free patient therapy.

DETAILED DESCRIPTION

Figure 1A:
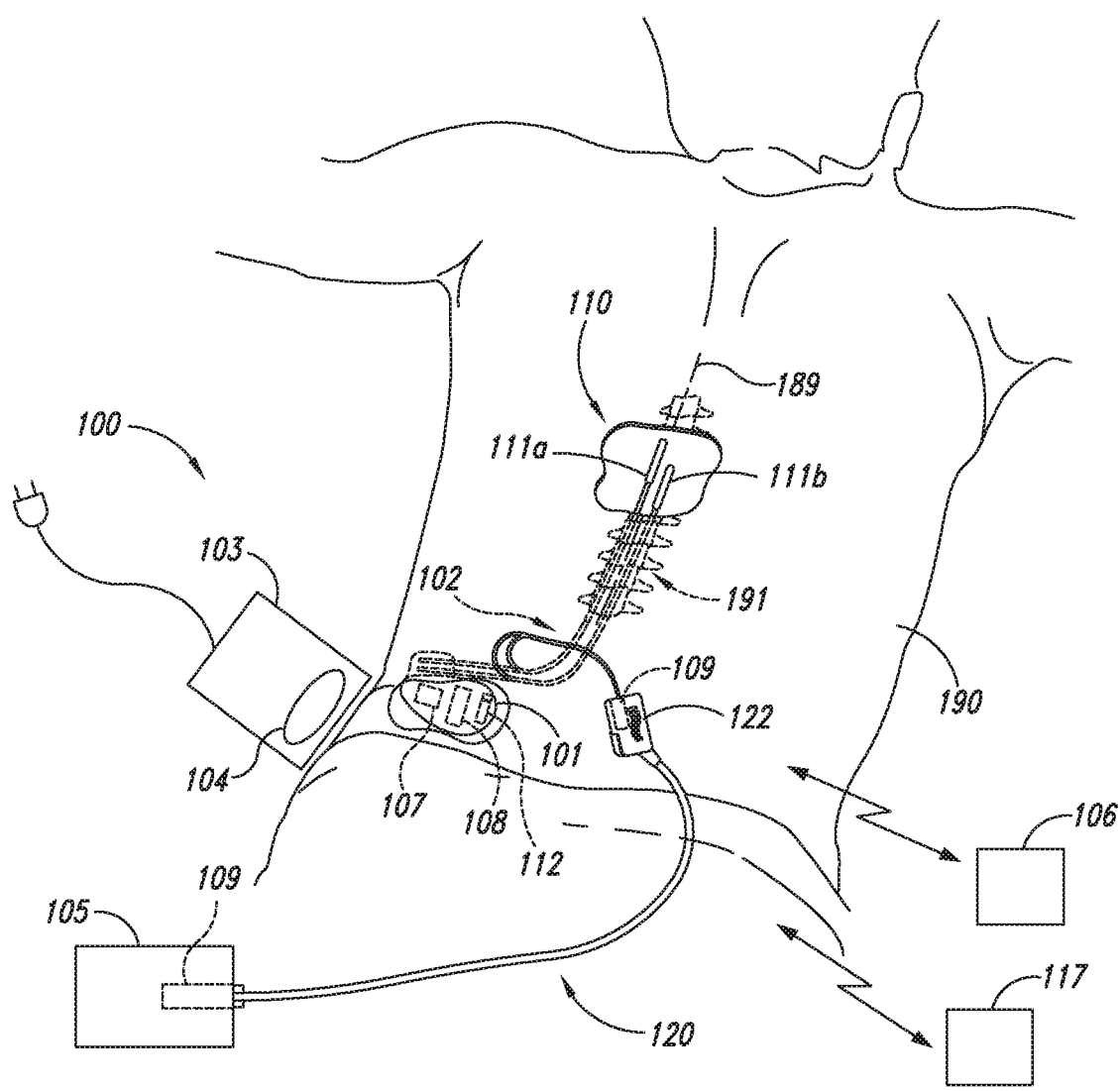
FIG. 1A is a partially schematic illustration of an implantable spinal cord modulation system positioned at the spine to deliver therapeutic signals in accordance with embodiments of the present technology.

The present technology is directed generally to systems and methods for enhancing usage characteristics of an implantable pulse generator (IPG) battery, which is used in part to deliver electrical signals (also referred to herein as "therapy signals") to provide patient treatment via spinal cord stimulation (SCS) and/or other techniques. For example, in some embodiments, the present technology includes a method of automatically adjusting, in a closed loop manner, the value of an electrical signal parameter. The adjusted parameter can include the voltage supplied to an electrical signal generating circuit of an IPG. The method can comprise adjusting the value of the electrical signal parameter (e.g., the supply voltage) until receiving an indication that a threshold break has occurred. The threshold break can correspond to the value of the electrical signal parameter passing below a threshold value, e.g., a value determined to be at or above the minimum value necessary to provide effective therapy to the patient. Based at least in part on the threshold value of the threshold break, the method can further comprise increasing the electrical signal parameter by a step size and thereafter adjusting (e.g., decreasing) the electrical signal parameter until a subsequent threshold break occurs, e.g., in a subsequent iteration. Each subsequent iteration can decrease the difference between the supplied electrical signal parameter and a minimum electrical signal parameter needed to deliver adequate therapy treatment to the patient. Accordingly, some embodiments of the present technology can enhance usage characteristics of an IPG to operate the battery in a more efficient manner and/or decrease the amount of unnecessary power loss therefrom.

In some embodiments, such as the particular example described above, the iterative process is based on the supply voltage passing below a threshold value. In some embodiments, the iterative process can be based on a parameter value exceeding a threshold value. Accordingly, unless otherwise specified, the terms "threshold break" and the like are used herein to refer to a parameter hitting or passing through a threshold value from above or below.

General aspects of the environments in which the disclosed technology operates are described below under Heading 1.0 ("Overview") with reference to FIGS. 1A, 1B, 2A and 2B. Some embodiments of the technology are described further under Heading 2.0 ("Representative Embodiments") with reference to FIGS. 3-5. While the present technology is described in the environment of SCS, one with skill in the art would recognize that one or more aspects of the present technology are applicable to other, non-SCS implantable devices; e.g., more generally, implantable neurostimulators for treatment of one or more patient indications.

1.0 Overview

Some representative examples of paresthesia-free SCS therapy systems include "high frequency" SCS systems. High frequency SCS systems can inhibit, reduce, and/or eliminate pain via waveforms with high frequency elements or components (e.g., portions having high fundamental frequencies), generally with reduced or eliminated side effects. Such side effects can include unwanted paresthesia, unwanted motor stimulation or blocking, unwanted pain or discomfort, and/or interference with sensory functions other than the targeted pain. In some embodiments, a patient may receive high frequency therapeutic signals with at least a portion of the therapy signal at a frequency of from about 1.2 kHz to about 100 kHz, or from about 1.5 kHz to about 50 kHz, or from about 3 kHz to about 20 kHz, or from about 5 kHz to about 15 kHz, or at frequencies of about 8 kHz, 9 kHz, or 10 kHz. These frequencies are significantly higher than the frequencies associated with conventional "low frequency" SCS, which are generally below 1,200 Hz, and more commonly below 100 Hz. Accordingly, modulation at these and other representative frequencies (e.g., from about 1.2 kHz to about 100 kHz) is occasionally referred to herein as "high frequency stimulation," "high frequency SCS," and/or "high frequency modulation."

FIG. 1A schematically illustrates a representative patient therapy system 100 for providing relief from chronic pain and/or other conditions, arranged relative to the general anatomy of a patient's spinal column 191. The system 100 can include a signal generator 101 (e.g., an implanted pulse generator or IPG), which may be implanted subcutaneously within a patient 190 and coupled to one or more signal delivery elements or devices 110. The signal delivery elements or devices 110 may be implanted within the patient 190, typically at or near the patient's spinal cord midline 189. The signal delivery elements 110 carry features for delivering therapy to the patient 190 after implantation. The signal generator 101 can be connected directly to the signal delivery devices 110, or it can be coupled to the signal delivery devices 110 via a signal link or lead extension 102. In some embodiments, the signal delivery devices 110 can include one or more elongated lead(s) or lead body or bodies 111 (identified individually as a first lead 111a and a second lead 111b). As used herein, the terms signal delivery device, lead, and/or lead body include any of a number of suitable substrates and/or support members that carry electrodes/devices for providing therapy signals to the patient 190. For example, the lead or leads 111 can include one or more electrodes or electrical contacts that direct electrical signals into the patient's tissue, e.g., to provide for therapeutic relief. In some embodiments, the signal delivery elements 110 can include structures other than a lead body (e.g., a paddle) that also direct electrical signals and/or other types of signals to the patient 190.

In some embodiments, one signal delivery device may be implanted on one side of the spinal cord midline 189, and a second signal delivery device may be implanted on the other side of the spinal cord midline 189. For example, the first and second leads 111a, 111b shown in FIG. 1A may be positioned just off the spinal cord midline 189 (e.g., about 1 mm offset) in opposing lateral directions so that the two leads 111a, 111b are spaced apart from each other by about 2 mm. In some embodiments, the leads 111 may be implanted at a vertebral level ranging from, for example, about T8 to about T12. In some embodiments, one or more signal delivery devices can be implanted at other vertebral levels, e.g., as disclosed in U.S. Pat. No. 9,327,121, which is incorporated by reference herein in its entirety.

The signal generator 101 can transmit signals (e.g., electrical signals) to the signal delivery elements 110 that up-regulate (e.g., excite) and/or down-regulate (e.g., block or suppress) target nerves. As used herein, and unless otherwise noted, the terms "modulate," "modulation," "stimulate," and "stimulation" refer generally to signals that have either type of the foregoing effects on the target nerves. The signal generator 101 can include a machine-readable (e.g., computer-readable) or controller-readable medium containing instructions for generating and transmitting suitable therapy signals. The signal generator 101 and/or other elements of the system 100 can include one or more processor(s) 107, memory unit(s) 108, and/or input/output device(s) 112. Accordingly, the process of providing modulation signals, providing guidance information for positioning the signal delivery devices 110, establishing battery charging and/or discharging parameters, and/or executing other associated functions can be performed by computer-executable instructions contained by, on or in computer-readable media located at the pulse generator 101 and/or other system components. Further, the pulse generator 101 and/or other system components may include dedicated hardware, firmware, and/or software for executing computer-executable instructions that, when executed, perform any one or more methods, processes, and/or sub-processes described herein; e.g., the methods, processes, and/or sub-processes described with reference to FIGS. 2-5 below. The dedicated hardware, firmware, and/or software also serve as "means for" performing the methods, processes, and/or sub-processes described herein. The signal generator 101 can also include multiple portions, elements, and/or subsystems (e.g., for directing signals in accordance with multiple signal delivery parameters), carried in a single housing, as shown in FIG. 1A, or in multiple housings.

The signal generator 101 can also receive and respond to an input signal received from one or more sources. The input signals can direct or influence the manner in which the therapy, charging, and/or process instructions are selected, executed, updated, and/or otherwise performed. The input signals can be received from one or more sensors (e.g., an input device 112 shown schematically in FIG. 1A for purposes of illustration) that are carried by the signal generator 101 and/or distributed outside the signal generator 101 (e.g., at other patient locations) while still communicating with the signal generator 101. The sensors and/or other input devices 112 can provide inputs that depend on or reflect patient state (e.g., patient position, patient posture, and/or patient activity level), and/or inputs that are patient-independent (e.g., time). Still further details are included in U.S. Pat. No. 8,355,797, incorporated by reference herein in its entirety.

In some embodiments, the signal generator 101 and/or signal delivery devices 110 can obtain power to generate the therapy signals from an external power source 103. In some embodiments, for example, the external power source 103 can by-pass an implanted signal generator and generate a therapy signal directly at the signal delivery devices 110 (or via signal relay components). The external power source 103 can transmit power to the implanted signal generator 101 and/or directly to the signal delivery devices 110 using electromagnetic induction (e.g., RF signals). For example, the external power source 103 can include an external coil 104 that communicates with a corresponding internal coil (not shown) within the implantable signal generator 101, signal delivery devices 110, and/or a power relay component (not shown). The external power source 103 can be portable for ease of use.

In some embodiments, the signal generator 101 can obtain the power to generate therapy signals from an internal power source, in addition to or in lieu of the external power source 103. For example, the implanted signal generator 101 can include a non-rechargeable battery or a rechargeable battery to provide such power. When the internal power source includes a rechargeable battery, the external power source 103 can be used to recharge the battery. The external power source 103 can in turn be recharged via a suitable power source (e.g., conventional wall power).

During at least some procedures, an external stimulator or trial modulator 105 can be coupled to the signal delivery elements 110 during an initial procedure, prior to implanting the signal generator 101. For example, a practitioner (e.g., a physician and/or a company representative) can use the trial modulator 105 to vary the modulation parameters provided to the signal delivery elements 110 in real time, and select optimal or particularly efficacious parameters. These parameters can include the location from which the electrical signals are emitted, as well as the characteristics of the electrical signals provided to the signal delivery devices 110. In some embodiments, input is collected via the external stimulator or trial modulator and can be used by the clinician to help determine what parameters to vary. In a typical process, the practitioner uses a cable assembly 120 to temporarily connect the trial modulator 105 to the signal delivery device 110. The practitioner can test the efficacy of the signal delivery devices 110 in an initial position. The practitioner can then disconnect the cable assembly 120 (e.g., at a connector 122), reposition the signal delivery devices 110, and reapply the electrical signals. This process can be performed iteratively until the practitioner obtains the desired position for the signal delivery devices 110. Optionally, the practitioner may move the partially implanted signal delivery devices 110 without disconnecting the cable assembly 120. Furthermore, in some embodiments, the iterative process of repositioning the signal delivery devices 110 and/or varying the therapy parameters may not be performed.

The signal generator 101, the lead extension 102, the trial modulator 105 and/or the connector 122 can each include a receiving element 109. Accordingly, the receiving elements 109 can be patient implantable elements, or the receiving elements 109 can be integral with an external patient treatment element, device or component (e.g., the trial modulator 105 and/or the connector 122). The receiving elements 109 can be configured to facilitate a simple coupling and decoupling procedure between the signal delivery devices 110, the lead extension 102, the pulse generator 101, the trial modulator 105 and/or the connector 122. The receiving elements 109 can be at least generally similar in structure and function to those described in U.S. Patent Application Publication No. 2011/0071593, incorporated by reference herein in its entirety.

After the signal delivery elements 110 are implanted, the patient 190 can receive therapy via signals generated by the trial modulator 105, generally for a limited period of time. During this time, the patient wears the cable assembly 120 and the trial modulator 105 outside the body. Assuming the trial therapy is effective or shows the promise of being effective, the practitioner then replaces the trial modulator 105 with the implanted signal generator 101, and programs the signal generator 101 with therapy programs selected based on the experience gained during the trial period. Optionally, the practitioner can also replace the signal delivery elements 110. Once the implantable signal generator 101 has been positioned within the patient 190, the therapy programs provided by the signal generator 101 can still be updated remotely via a wireless physician's programmer 117 (e.g., a physician's laptop, a physician's remote or remote device, etc.) and/or a wireless patient programmer 106 (e.g., a patient's laptop, patients remote or remote device, etc.), Generally, the patient 190 has control over fewer parameters than does the practitioner. For example, the capability of the patient programmer 106 may be limited to starting and/or stopping the signal generator 101, and/or adjusting the signal amplitude. The patient programmer 106 may be configured to accept pain relief input as well as other variables, such as medication use.

In any of the foregoing embodiments, the parameters in accordance with which the signal generator 101 provides signals can be adjusted during portions of the therapy regimen. For example, the frequency, amplitude, pulse width, and/or signal delivery location can be adjusted in accordance with a pre-set therapy program, patient and/or physician inputs, and/or in a random or pseudorandom manner. Such parameter variations can be used to address a number of potential clinical situations, Certain aspects of the foregoing systems and methods may be simplified or eliminated in some embodiments of the present disclosure. Further aspects of these and other expected beneficial results are detailed in U.S. Pat. Nos. 9,327,121 (previously incorporated by reference), 8,712,533, and 9,592,388, and U.S. Patent Application Publication No, 2009/0204173, all of which are incorporated herein by reference in their entireties.

Figure 1B:
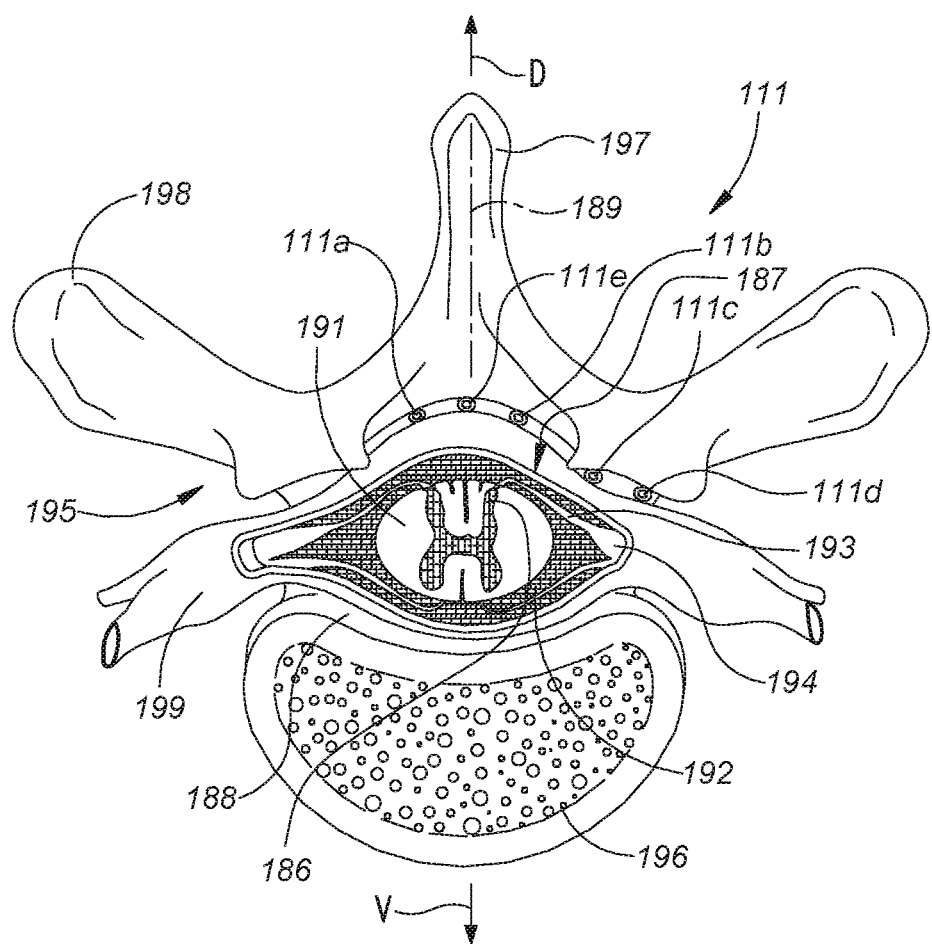
FIG. 1B is a partially schematic, cross-sectional illustration of a patient's spine, illustrating representative locations for implanted lead bodies in accordance with embodiments of the present technology.

FIG. 1B is a cross-sectional illustration of the spinal cord 191 and an adjacent vertebra 195 (based generally on information from Crossman and Neary, "Neuroanatomy," 1995 (published by Churchill Livingstone)), along with multiple leads 111 (shown as leads 111a-111e) implanted at representative locations. For purposes of illustration, multiple leads 111 are shown in FIG. 1B implanted in a single patient. In actual use, any given patient will likely receive fewer than all the leads 111 shown in FIG. 1B.

The spinal cord 191 is situated within a vertebral foramen 188, between a ventrally located ventral body 196 and a dorsally located transverse process 198 and spinous process 197. Arrows V and D identify the ventral and dorsal directions, respectively. The spinal cord 191 itself is located within the dura mater 199, which also surrounds portions of the nerves exiting the spinal cord 191, including the ventral roots 192, dorsal roots 193 and dorsal root ganglia 194. The dorsal roots 193 enter the spinal cord 191 at the dorsal root entry zone 187, and communicate with dorsal horn neurons located at the dorsal horn 186. In one embodiment, the first and second leads 111a, 111b are positioned just off the spinal cord midline 189 (e.g., about 1 mm. offset) in opposing lateral directions so that the two leads 111a, 111b are spaced apart from each other by about 2 mm, as discussed above. In other embodiments, a lead or pairs of leads can be positioned at other locations, e.g., toward the outer edge of the dorsal root entry zone 187 as shown by a third lead 111c, or at the dorsal root ganglia 194, as shown by a fourth lead 111d, or approximately at the spinal cord midline 189, as shown by a fifth lead 111e.

Figure 2A:
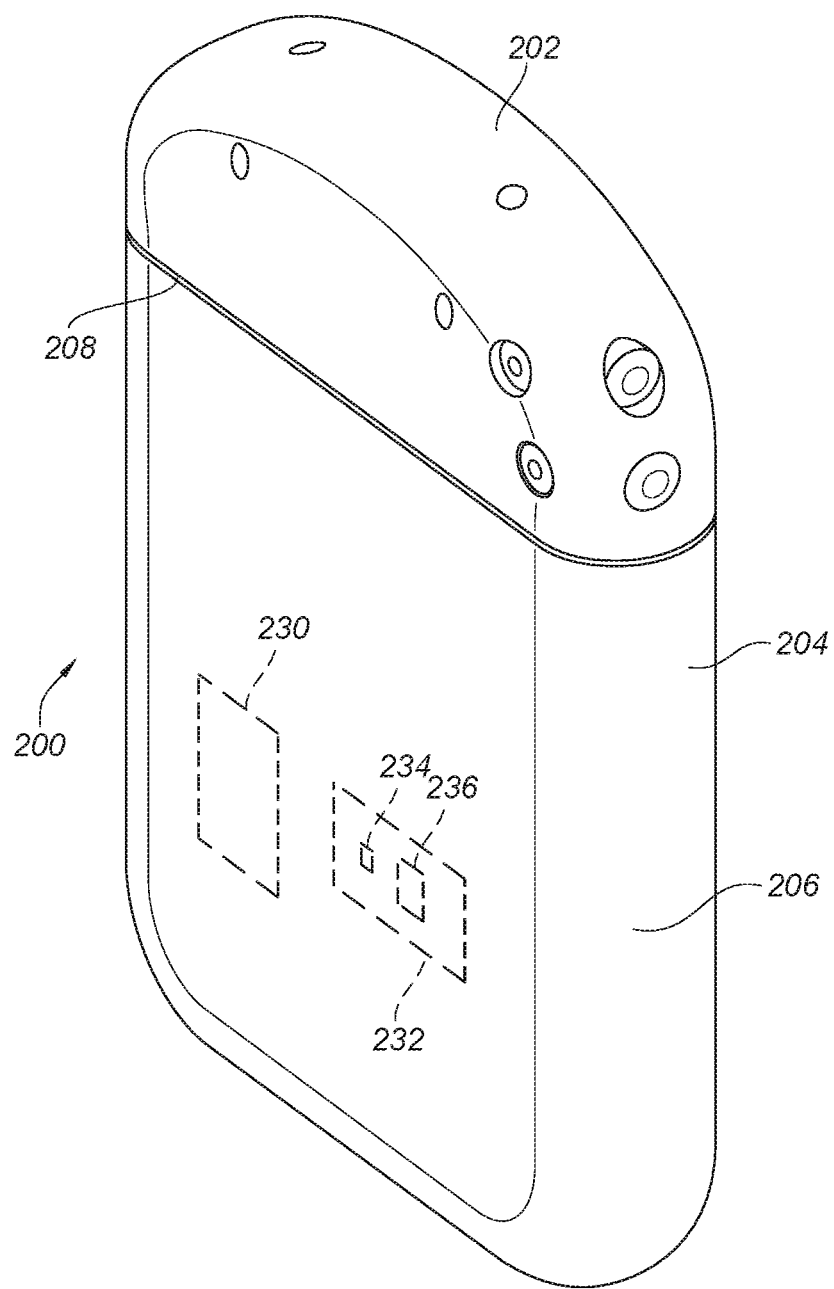
FIG. 2A is a partially schematic isometric view of an implantable signal generator having a molded header and a can configured in accordance with embodiments of the present technology.
Figure 2B:
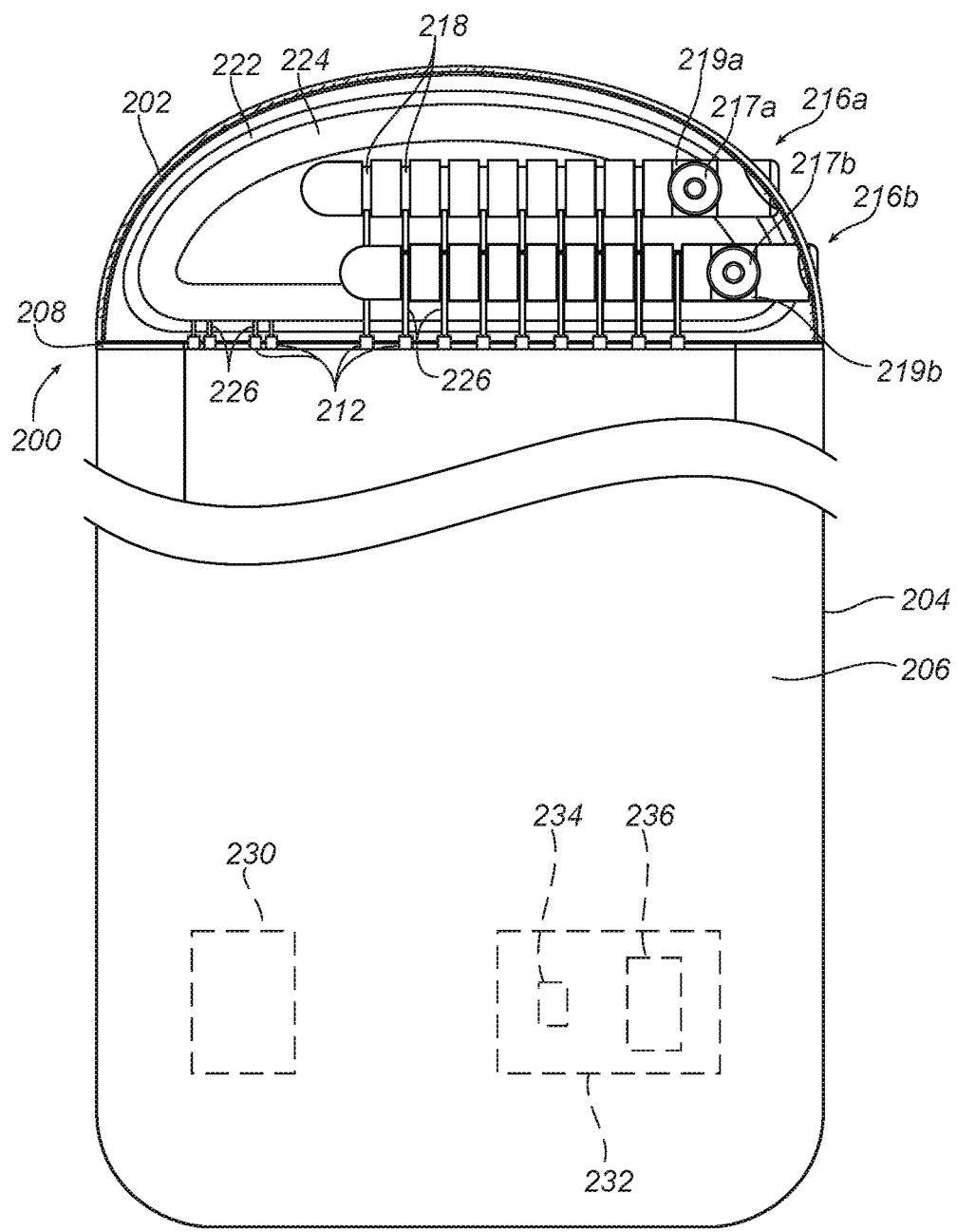
FIG. 2B is a partially cutaway side view of a portion of the implantable signal generator of FIG. 2A.

FIG. 2A is a partially schematic isometric view of an implantable signal generator 200 (e.g., an IPG), and FIG. 2B is a partially cutaway side view of a portion of the implantable signal generator 200. Referring first to FIGS. 2A, the signal generator 200 includes a header 202, and a can 204 attached to the header 202. The can 204 may include a shell 206 and a lid 208 positioned at least partially between the header 202 and the can 204. Referring next to FIG. 2B, the lid 208 can include a plurality of feed-throughs 212 for electrical communication between the header 202 and the can 204. The header 202 can carry a charging coil 224, a communication antenna 222, and one or more receiving elements 216. The receiving elements 216 can include a plurality of output terminals or contact assemblies 218 configured to provide electrical connections to the signal delivery devices 110 or the lead extension 102.

Multiple wires 226 can extend upwardly from the can 204 through the feed-throughs 212 and couple to (a) individual contact assemblies 218, (b) the communication antenna 222, or (c) the charging coil 224. The wires 226 can provide electrical connections between components within the header 202, e.g., the charging coil 224 and the communication antenna 222, and components within the can 204, e.g., a battery 230, a controller 232, etc. The battery 230 can be electrically coupled to the controller 232 and the output terminals or contact assemblies 218 to provide electrical power to the implantable signal generator 200 via the receiving elements 216, The battery 230 can be recharged via an electrical coupling to the charging coil 224. The controller 232 can be electrically coupled to the contact assemblies 218 and the battery 230, and can include a processor 234, memory 236, electronic circuitry, and other electronic components for controlling and/or operating the implantable signal generator 200. In operation, the charging coil 224 can convert electromagnetic energy (e.g., a magnetic flux) into electrical current to charge the battery 230. The communication antenna 222 can receive signals associated with operating and/or controlling the implantable signal generator 200, For example, control signals to update operating parameters (e.g., the frequency, amplitude and/or duration of modulation signals) for the implantable signal generator 200 can be received by the communications antenna 222 and sent to the controller 232. The controller 232 can control the delivery of electrical power to the receiving elements 216, The header 202 includes a first access seal 217a and a second access seal 217b (collectively referred to as the access seals 217). The access seals 217 include a self-sealing entrance point to provide access for a tool (e.g., a screwdriver) to secure a connection (e.g., a screw) to the signal delivery device 110 (FIG. 1A) or the lead extension 102 (FIG. 1A) via the set-screw blocks 219. The access seals 217 can be formed from a pliable silicone or other suitable material such that the tool can pass through and expand the entrance point. When the tool is withdrawn, the entrance point can automatically close to reduce or eliminate the possibility of any foreign material (e.g., blood or other bodily fluids) subsequently entering into the header 202.

Computer readable instructions contained in the memory 236 can include operating parameters and instructions to control the operation of the implantable signal generator 200. Specifically, the implantable signal generator 200 can include battery charging integrated circuits (IC) to monitor battery status and protect the battery against overcharging and/or over-discharging, thereby decreasing the chance of irreversible damage to the battery. The battery charging IC can comprise battery protection circuitry that includes (a) battery-charging circuitry electrically coupling the battery to power sources and/or other components configured to charge the battery, and (b) battery-load circuitry electrically coupling the battery to the implantable signal generator 200 and/or other components configured to discharge or drain the battery. In some embodiments, the battery charging IC can include one or more switches, e.g., field effect transistors (FETs), set to automatically open and/or close in order to maintain the charging and discharging parameter values (e.g., voltages) of the battery within preset battery operating parameter limits. The battery charging IC can similarly include one or more fuses set to maintain the charging and discharging current values of the battery within preset current parameter limits. As described in further detail below, the battery protection circuitry can be set to ensure operating battery voltage and/or current do not exceed or fall below corresponding thresholds.

2.0 Representative Embodiments

Establishing Battery Charging and Discharging Parameters to Extend Battery Life Systems of the type described above with reference to FIGS. 1A-2B can include IPGs having rechargeable batteries or other rechargeable power sources that are periodically recharged with an external charger. Over the course of a given therapeutic regimen, the patient and/or the practitioner may change the parameters in accordance with which the electrical signals are delivered to the patient. As the parameters change, the rate at which electrical current is drawn or drained from the battery can also change. In addition, different patients may charge their batteries in accordance with different schedules, and/or may vary in the consistency with which they adhere to such schedules. Still further, the characteristics of the rechargeable battery can change over the course of time. For example, the overall charge capacity (C) of the battery will typically decrease over time, e.g., due to chemical degradation. Techniques in accordance with the present technology, described further below, can tailor the manner in which the battery is charged and/or discharged by taking into account one or more of the foregoing variables to increase the usable life of the battery, and/or can be applied generally, e.g., without patient specific parameters.

As previously described, irreversible damage of the battery components, e.g., the negative electrode or electrolyte, can occur if the battery is over-discharged below or over-charged above particular thresholds. For example, over-discharging the battery below a lower damage threshold (LDT), and/or overcharging the battery above an upper damage threshold (UDT) can cause "thermal runaway," thereby potentially causing at least a portion of the battery components to break down. In some embodiments, the LDT for a lithium-ion battery having a nominal voltage output of approximately 3.6V, may be at approximately 2.75V+/−0.2V, and the UDT for lithium-ion battery may be at approximately 4.1V+/−0.2V. In lieu of or in addition to the voltage thresholds, the LDT and/or UDT can be based on current. The present technology provides methods for establishing charge parameters for a battery-powered implantable medical device to avoid over-discharging a battery below the LDT and/or overcharging a battery above the UDT, while also maintaining efficient charging parameters for convenience of the patient.

In some embodiments, there is provided a method for establishing charge parameters for a battery-powered implantable medical device, wherein the battery is charged at a constant primary charge rate (PCR) over the normal operating range of the battery. The PCR is intended to represent a charge rate considered to most efficiently charge the battery. For example, the PCR can correspond to the highest charge rate that maintains a minimum level of risk that damage to the battery will occur during charging. In one non-limiting example, the battery may be charged at a PCR of approximately C/2 (e.g., half of the battery capacity) at least within a normal operating range of the battery. In some embodiments, the PCR may be C13, C/4, etc.

In some embodiments, the normal operating range of the battery can be from (a) a lower operating threshold (LOT) set above, or slightly above (e.g., less than 10% above) the LDT, to an upper operating threshold (UOT) set below (e.g., slightly below) the UDT. For a battery having a nominal output voltage of approximately 3.6V, the LOT can vary from approximately 3.1V to approximately 3.3V, and the UOT can vary from approximately 3.9V to approximately 4.1V. The LOT and UOT can prevent the battery from reaching the LDT and UDT, respectively, and thereby prevent or inhibit irreversible damage to the battery. As the battery approaches, but does not surpass, one of the LOT or the UOT, battery protection circuitry of the IPG can maintain the charging rate at the PCR. As such, the battery protection circuitry may not include or transition to the trickle charge rate previously described. One advantage of having a constant PCR in combination with battery charging circuitry is that, compared to a traditional IPG that automatically switches to a trickle charge rate, the battery can experience a faster charge while still maintaining protection to prevent irreversible damage to the battery. As a result, the present technology makes more effective use of the patient's time, as the patient does not need to wait for the additional time needed during the "trickle charge" phase to fully-charge the battery.

Unlike traditional batteries that transition to a trickle charge rate as battery threshold limits are approached, the battery charging IC of the present technology can be configured to automatically disconnect the battery from battery-charging circuitry or the battery-load circuitry. For example, the battery protection circuitry can automatically disconnect the battery from the battery-charging circuitry once the UOT is reached or nearly reached to prevent or inhibit the battery voltage from reaching or surpassing the UDT. In some embodiments, power transmitted to the battery will not be received, and thus will not affect the operating voltage or operating current of the battery. As such, when the battery reaches or nearly reaches the UOT and is thus considered fully charged, any patient-initiated further charge will be prohibited via the battery charging IC, or more specifically by opening switches and/or fuses of the battery charging circuitry.

Similarly, as the battery discharges and the LOT is reached or nearly reached, the battery protection circuitry can automatically disconnect at least a portion of the battery from the battery-load circuitry to prevent or inhibit the battery voltage from reaching or falling below the LDT. In some embodiments, a load or a portion of the load being drawn from the battery ceases. For example, in some embodiments, certain functions of the IPG, e.g., signal delivery functions and telemetry functions, may cease. As such, when the battery charge reaches or nearly reaches the LOT and is thus considered discharged to a minimum operating range, any further load request made to the battery may be ignored More specifically, the switches and/or fuses of the battery charging circuitry may open once the battery charge reaches the LOT, thereby causing the IPG to lose at least a portion of its ability to further drain the battery. In some embodiments, while certain functions of the IPG may cease, other functions, e.g., a clock function, of the IPG may continue to be operational, thereby allowing the patient and/or operator to monitor diagnostics of the IPG even after the battery charge has discharged at or below the LOT. As a result, these other functions of the IPG that continue to be operational may cause the battery charge to further discharge, but at a slower rate. For example, once the LOT is reached, the current draw of the battery may be decreased, thereby allowing the battery charge to remain above the LDT or another threshold limit for a few weeks.

In some embodiments wherein the battery is discharging and approaching the LOT, the battery charging IC may include a second lower operating threshold (SLOT) between the LOT and LDT. The SLOT may function as a further precaution to ensure the battery charge does not reach the LDT, and can vary within a range from approximately 2.8V+/−0.2V to approximately 3.1V+/−0.2V, or within a narrower or broader range depending on the corresponding LOT and LDT. As previously stated, once the LOT is reached, certain functions of the IPG may cease. Once the SLOT is reached, the IPG may then be completely disconnected from remaining functions of the IPG, and placed into a hibernation state intended to prevent the battery from discharging further. As such, the battery may continue to discharge, but at an even slower rate than the discharge rate after the LOT is reached. Once the SLOT is reached, the current draw of the battery may be at an absolute minimum, and in some embodiments, can allow the battery charge to remain above the LDT for approximately 6-9 months or longer, depending on the margin between the SLOT and LDT.

The LDT, SLOT, LOT, UOT and UDT can each be set such that a minimum margin is maintained between a neighboring threshold. For example, the SLOT may be set at a preset margin, e.g., 1%, 5%, 10%, etc., above the LDT, and the LOT may be set at a preset margin, e.g., 1%, 5%, 10%, etc., above the SLOT. Similarly, the UOT may be set at a preset margin, e.g., 1%, 5%, 10%, etc., below the UDT. Naturally, a higher margin better ensures that the LDT and/or UDT will not be reached, and that irreversible damage to the battery will not occur. The preset LOT-LDT margin and the UOT-UDT margin, can be the same, e.g., both can be set to 5%, or they can differ, e.g., the LOT-LDT margin can be set to 10% and the UOT-UDT margin can be set to 5%. Setting the LOT-LCAT margin higher may be preferred to ensure any disruption of patient therapy is avoided. Also, setting the LOT-LDT margin higher can be beneficial because of the inherent self-discharge of batteries that can cause the operating voltage to further decrease even after the battery charging circuitry electrically disconnects the battery from the surrounding system components.

One feature of at least some embodiments is that the processes for establishing and/or adjusting the charge and/or discharge parameters can be automated. An advantage of this feature is that it can reduce or eliminate the effort on the part of the patient and/or the practitioner and/or the company representative to achieve the benefits of tailored charge/discharge parameters. Still another advantage of the foregoing features is that, in some embodiments, the patients perception of the consistency of the system can be improved. For example, by automatically providing and adjusting (as needed) the margins within which the IPG battery operates, the patient will be less likely to over-discharge the battery.

Another feature of at least some embodiments is that processes for establishing and/or adjusting the charge and/or discharge parameters can be tailored, adjusted, determined, calculated, set, or otherwise established in a manner that reflects patient-specific and/or battery-specific characteristics. The battery characteristics can include the age of the battery, the number of charge cycles undergone by the battery, the total amount of charge delivered by the battery (e.g., over many charge cycles), and/or other aspects of the battery that may vary from one patient's IPG to another patient's IPG. As another example, an older battery and/or a battery that has been charged and discharged many times will typically have a lower total charge capacity than a battery that is new and/or has undergone fewer charge/discharge cycles. The data corresponding to these characteristics can be stored at the IPG and updated periodically. For example, the IPG can store the manufacture date of the battery. Each time the battery is charged, the IPG can increment a battery charge counter. Further aspects of these and other expected beneficial results are detailed in U.S. Patent Application Publication No. 2016/0114171 which is incorporated by reference herein in its entirety.

Enhancing Usage Characteristics of an IPG Battery

Figure 3:
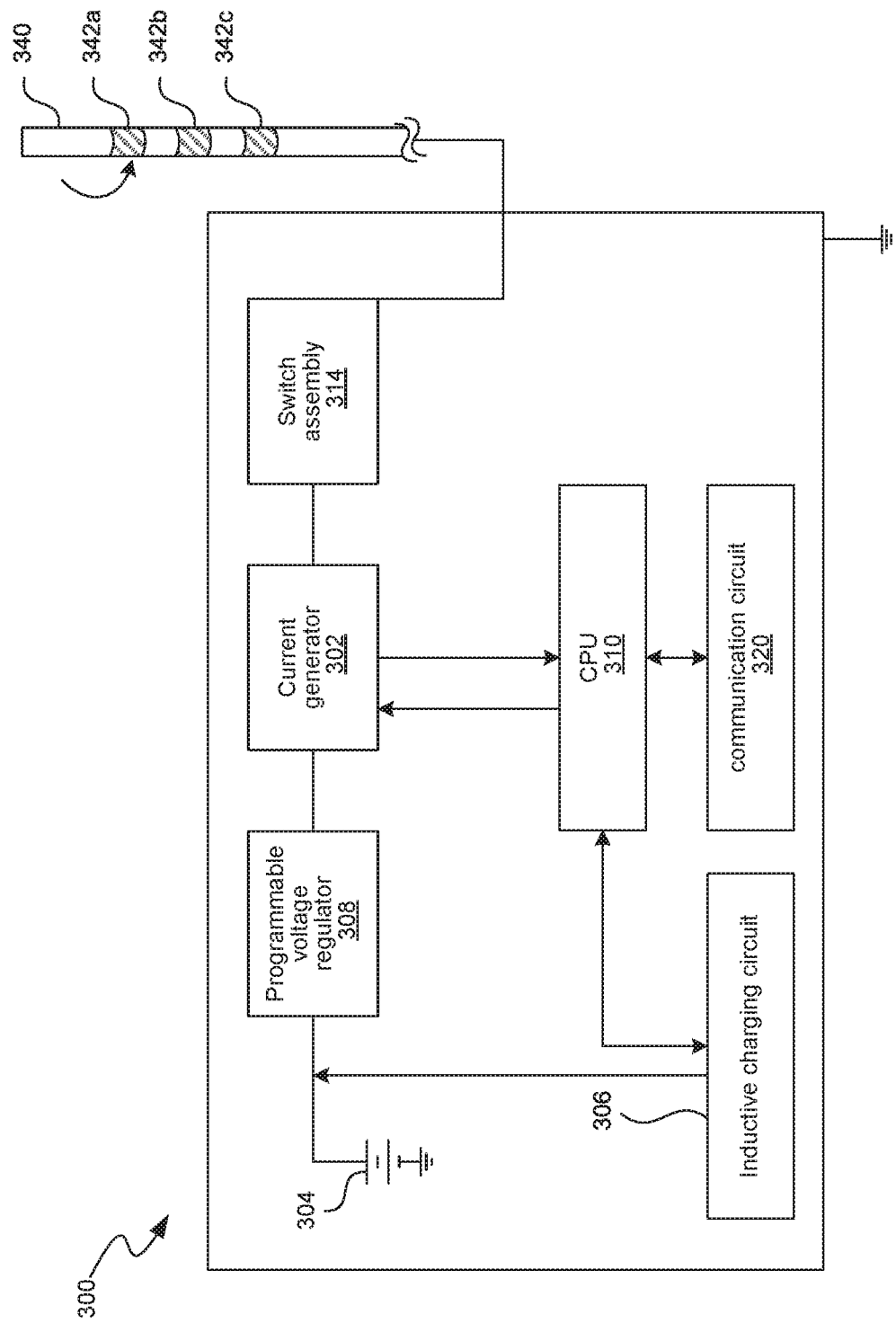
FIG. 3 is a circuit diagram of a therapeutic current-generating circuit that includes a voltage monitoring circuit in accordance with embodiments of the present technology.

FIG. 3 shows a simplified block diagram of an implantable therapeutic device 300 (e.g., an IPG) configured in accordance with an some embodiments of the present technology. The implantable device 300 includes a current-generating circuit 302 (labelled current generator) that produces therapeutic currents for one or more electrode leads 340 or other signal delivery device(s). The therapeutic device further includes a rechargeable battery 304 and an inductive charging circuit 306 that is used to recharge the battery 304 from an external charger (e.g., external power source 103 from FIG. 1A). Alternatively, the battery 304 may be a single-use battery that must be periodically replaced. The therapeutic device also includes a logic circuit or processor (CPU) 310 (e.g., a microprocessor, a microcontroller, digital signal processor FPGA, ASIC or the like). Voltage from the battery 304 is supplied to a programmable voltage regulator 308 that produces a variable supply voltage to the current-generating circuit 302 under the control of the processor 310. In some embodiments, the battery 304 is a lithium-ion battery that produces a voltage of approximately 3.2 volts when fully charged. The programmable voltage regulator 308 can increase this voltage to a higher level (e.g., 4-20 volts) or can decrease the voltage, e.g., down to approximately 2.0 volts or lower.

In some embodiments, the processor 310 is programmed to send signals to the programmable voltage regulator 308 to adjust the voltage supplied to the current generating circuit 302 so that the current generating circuit 302 can supply a requested current to the electrodes on the lead(s) 340 but not supply a voltage that is so high that battery power is wasted.

A programmable switch assembly 314 in the implantable device 300 is used to configure connections to the electrodes 342*a-c* (collectively "electrodes 342") on the leads 340 in order to control how the requested current is delivered to the patient. The switch assembly 314 is controlled by the processor 310 so that currents can be delivered between any of the electrodes 342 on the lead (e.g., between one or more "anode" contacts and one or more "cathode" contacts to operate the device in a bi-polar or other multi-polar manner). Alternatively, the programmable switch assembly 314 can configure the connections to the contacts so that currents flow between one or more of the contacts 342 and a remote common electrode or contact (such as the case of the implantable device) in order to operate the contacts 342 in a uni-polar manner.

In some embodiments, the implantable device 300 includes a wireless communication circuit 320 that transmits and receives signals from an external programmer (e.g., the patient programmer 106, the physician's programmer 117 shown in FIG. 1A), in order to control the therapies that are delivered to the patient, to supply a doctor or technician with information about the operation of the device, to update the operating program or parameters of the device and for other uses. Additional details of current generator circuits and related information are provided in U.S. Patent Application Publication No. 2017/0197079, which is incorporated by reference herein in its entirety.

As discussed above, it is desirable that the voltage supplied by the programmable voltage regulator 308 is sufficient to allow the current-generating circuit 302 to generate the requested currents for delivery to the contacts. On the other hand, if the voltage supplied to the current-generating circuit is more than the voltage needed, battery power is wasted and battery power will be depleted unnecessarily. The present technology includes methods and systems configured to manage these competing technologies.

Figure 4:
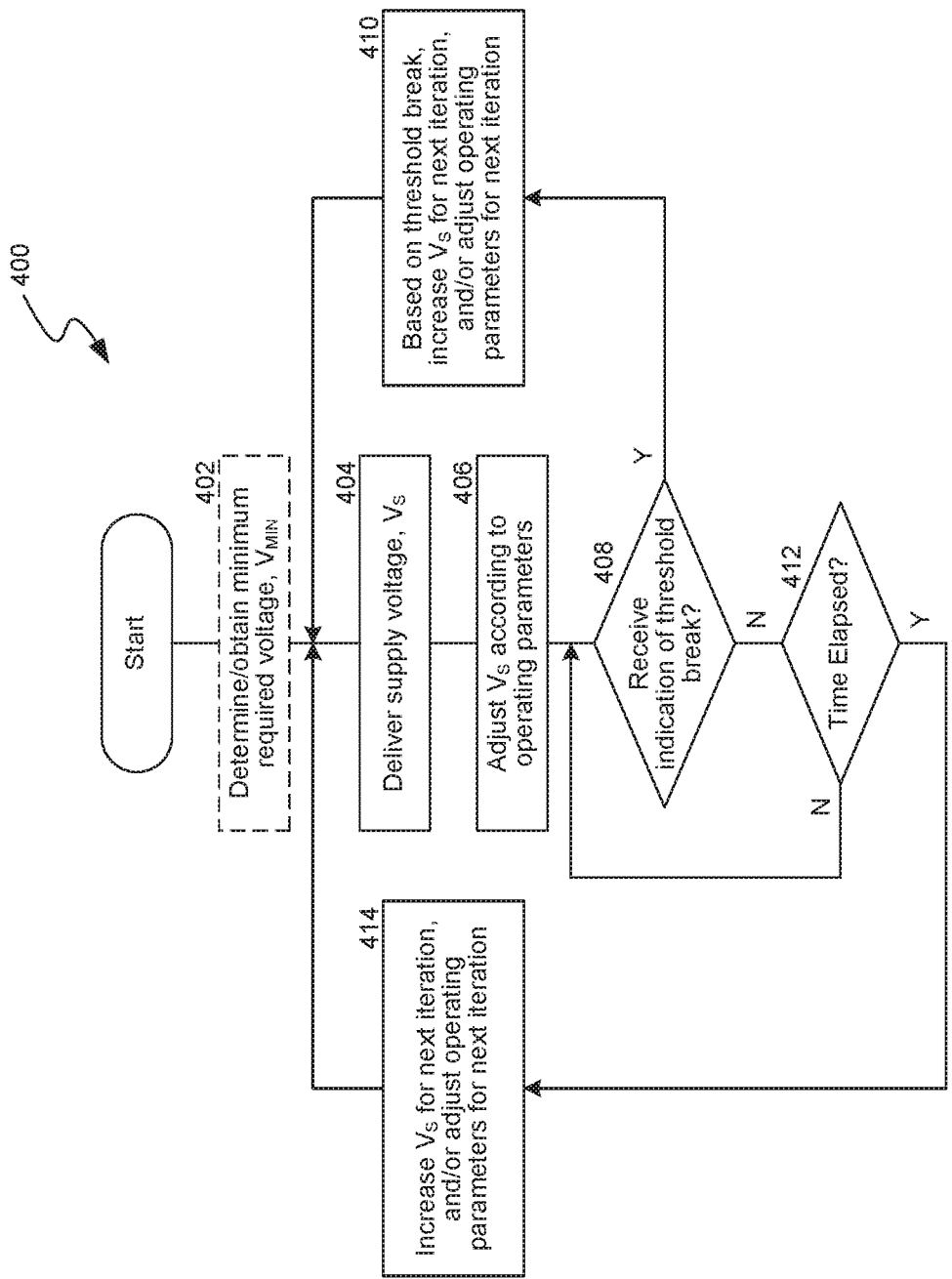
FIG. 4 is a flow diagram illustrating a representative process for automatically adjusting an electrical signal in accordance with embodiments of the present technology.

FIG. 4 is a flow diagram illustrating a representative process 400 for enhancing usage characteristics of an IPG battery in accordance with some embodiments of the present technology. Process 400 generally comprises operations for iteratively tuning a supplied voltage, $V_S$, to minimize its difference from a minimum required voltage, $V_{MIN}$, needed to deliver adequate therapy treatment to the patient. In a first iteration of a closed loop, the system causes $V_S$ to approach $V_{MIN}$ according to a set of operating parameters until $V_S$ is equal to or less than a threshold value, $V_{TH}$, which is above $V_{MIN}$. A threshold break occurs at the point in time when $V_S$ is approximately equal to or slightly below $V_{TH}$. Based on this threshold break, the system can adjust $V_S$ (e.g., by a step size) and operating parameters for a subsequent iteration of the closed loop. This process can then be repeated, with updated $V_S$ values and updated operating parameters for subsequent iterations being based on one or more of the previous threshold breaks.

Generally speaking, this process allows $V_S$ to track $V_{MIN}$ to reduce or eliminate power loss resulting from a higher than necessary $V_S$.

Process portion 402 includes determining and/or obtaining a minimum operating voltage, $V_{MIN}$. As previously described, $V_{MIN}$ can correspond to the minimum voltage that needs to be supplied to a current-generating circuit for it to deliver a requested current to electrodes on one or more leads connected to the IPG. $V_{MIN}$ and/or the requested current from the current generating circuit are functions of impedance and can vary based on multiple factors, including the particular therapy requested or delivered at a given time, patient movement, patient posture, patient activity level, etc. In some embodiments, determining $V_{MIN}$ on a continuous basis can cause significant power to be drawn from the IPG battery. Accordingly, in some embodiments, process portion 402 may be omitted from the process 400.

Process portion 404 includes delivering or supplying a supply voltage, $V_S$, to the current-generating circuit, which then uses $V_S$ to deliver a requested current to the patient as therapy. When a therapy session is first initiated, the specific value of $V_{MIN}$ may not be known, and thus $V_S$ may be supplied at a default value that is high enough to ensure it is above most or all possible $V_{MIN}$ values. The therapy (e.g., at the requested current) can then be delivered to the patient. As such, $V_S$ may initially operate at a level (e.g., 10V) that is significantly above $V_{MIN}$. Alternatively, in some embodiments, $V_S$ may correspond to a particular voltage from a previous therapy treatment for that patient and the particular impedance. For example, if the processor associated with the IPG assimilates an impedance profile for the current treatment with a similar impedance profile from a previous treatment, the processor can input the $V_S$ value previously used as the initial $V_S$ value for the current treatment. In some embodiments, the $V_S$ value may be accessed via a database of impedance profiles corresponding to that particular patient or other patients who had similar therapy treatments. Using these previous $V_S$ values can aid in reducing the excess power loss typically seen when a therapy treatment session is initiated at a high $V_S$ level.

Process portion 406 includes adjusting $V_S$ according to a set of operating parameters. The operating parameters, for example, can include a rate (e.g., volts/millisecond) at which $V_S$ is to be increased or decreased in order to cause a threshold break, as previously described. As discussed above, when a therapy session is first initiated, $V_{MIN}$ may not be known, and thus the relationship between $V_{MIN}$ and $V_S$ may also not be known. As such, the initial operating parameters for the first iteration of the closed loop may be default values that, for example, result in $V_S$ decreasing along a negative slope until $V_S$ approximately equals or falls below the threshold value, $V_{TH}$. In some embodiments, the operating parameters may be based on operating values from previous treatments, and accordingly the process 400 may reference the database of impedance profiles, as previously described. As explained in further detail with reference to FIG. 5, the operating parameters for a single iteration (e.g., process portions 404, 406, 408, and 410) of a closed loop may be based on operating parameters from an immediately previous iteration or multiple previous iterations (e.g., the two preceding iterations or three preceding iterations).

In some embodiments, process portion 406 can include adjusting (e.g., increasing or decreasing) or holding a $V_S$ value until and if an indication of a threshold break is received (process portion 408) by the system, or until a preset time has elapsed without a threshold break having occurred (process portion 412). As previously mentioned, a threshold break can include a moment in time at which $V_S$ equals or falls below $V_{TH}$. For example, if $V_{MIN}$ is equal to 2V, and the system includes a preferred operating margin of 0.5V, then the threshold limit would be 2.5V. As such, the system would receive an indication of a threshold break if and when $V_S$ falls below the threshold limit of 2.5V as $V_S$ is being decreased according to process portion 406. The characteristics accompanying the threshold break (e.g., the $V_S$ value at the threshold break, the time elapsed since the previous threshold break, etc.), in addition to the characteristics of the previous threshold breaks, can then provide a basis for altering $V_S$ and/or the operating parameters (e.g., process portion 410) for a subsequent iteration of the closed loop. As such, in some embodiments, if and when an indication of a threshold break is received, new values for $V_S$ and the operating parameters can be sent to the processor to be used in the subsequent iteration. For example, process portion 410 includes adjusting $V_S$ and/or the operating parameters for the process portion 404 for the subsequent iteration. In practice, when the next iteration is initiated (e.g., after a threshold break or elapsed time), the $V_S$ profile will experience an initial step corresponding to the newly adjusted $V_S$ value, followed by an increase, decrease, or hold of $V_S$ corresponding to the newly adjusted operating parameters. With each iterative adjustment made to the $V_S$ value and the operating parameters, the voltage difference between $V_{MIN}$ and $V_S$ can be decreased at least because the profile of $V_{MIN}$ becomes better understood and $V_S$ can be adjusted to more closely reflect $V_{MIN}$.

In some embodiments, a threshold break may not occur within an elapsed time. In such embodiments, after the elapsed time since adjusting $V_S$ via process portion 406, the process 400 can proceed to process portion 414 (process portion 412). Process portion 412 can help ensure a minimum time has passed before any subsequent closed loop begins. In some embodiments where the process 400 proceeds to process portion 404 via process portion 414 (i.e., without receiving indication of a threshold break at process portion 408), $V_S$ and/or the operating parameters may be adjusted in predetermined manner for the next iteration.

Figure 5:
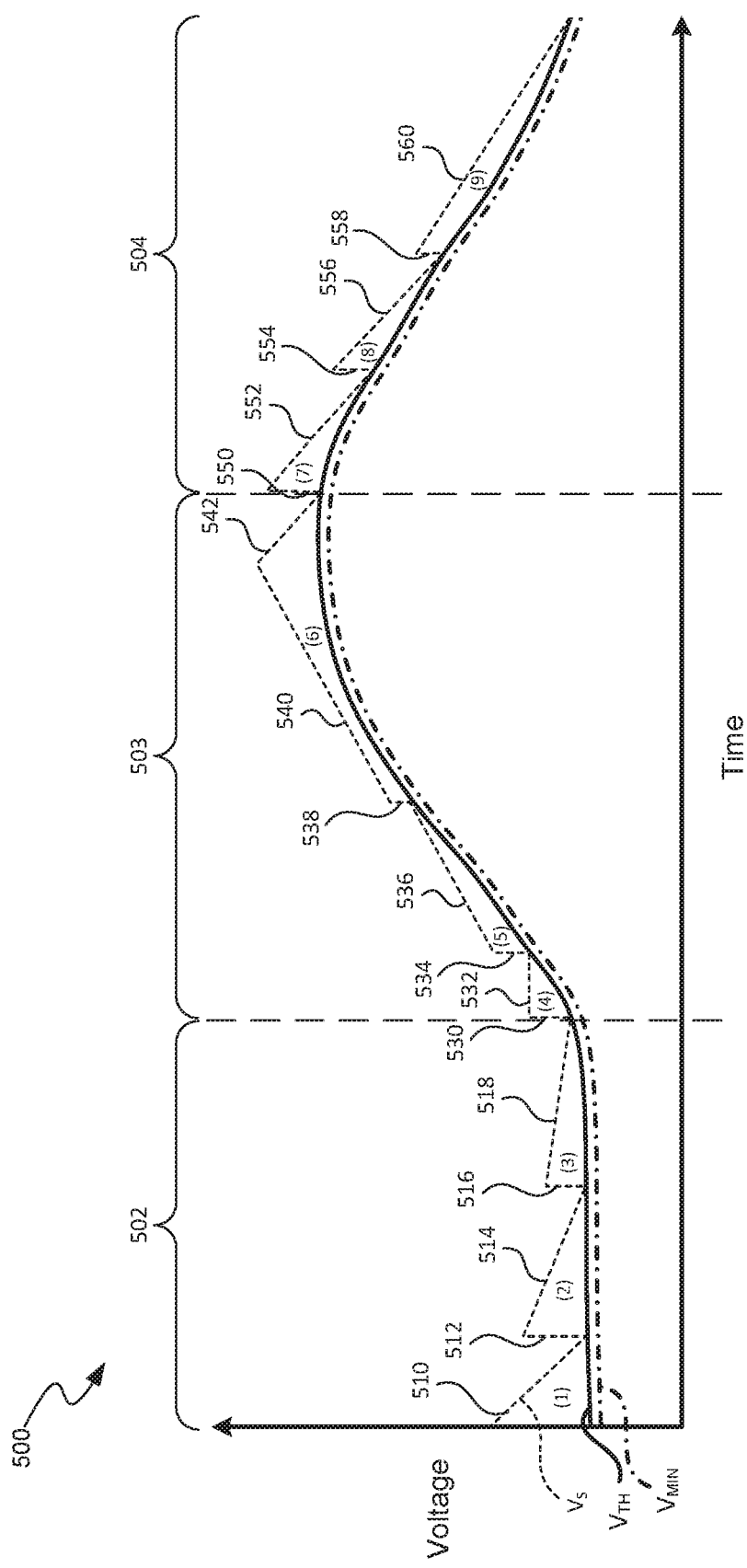
FIG. 5 illustrates results from a simulation of the process shown in FIG. 4.

FIG. 5 illustrates a plot 500 depicting a simulation of a representative process described in FIG. 4. The y-axis corresponds to voltage (e.g., measured voltage), and the x-axis corresponds to time (e.g. milliseconds). A first line (shown in dot-dash format) corresponds to $V_{MIN}$, a second line (shown solid) corresponds to $V_{TH}$, and a third line (shown dashed) corresponds to $V_S$. As previously described with reference to FIG. 4, $V_S$ can be continuously adjusted according to the iterative operations of (1) supplying $V_S$ for a first iteration of a closed loop, (2) adjusting $V_S$ according to operating parameters for the first iteration, (3) receiving an indication of a threshold break resulting from $V_S$ equaling or falling below $V_{TH}$, (4) after the threshold break, determining and adjusting $V_S$ and operating parameters for a subsequent iteration of the closed loop, and (5) iteratively repeating the operations of (1), (2), (3), and (4) as therapy continues to be delivered to the patient. As shown in FIG. 5, the simulation illustrated includes a first portion 502 having a relatively steady $V_{MIN}$ profile, a second portion 503 having an increasing $V_{MIN}$ profile, and a third portion 504 having a decreasing $V_{MIN}$ profile. In some embodiments, each of these portions 502, 503, 504 can correspond to different algorithms used to determine the corresponding supply voltage and operating parameters.

Starting at the first iteration (1) shown in FIG. 5, $V_S$ is initially set to a default value that is greater than $V_{TH}$ and $V_{MIN}$, and then decreases along path 510 according to a set of default operating parameters. Upon reaching $V_{TH}$, the system indicates a first threshold break. As previously described, the threshold break can correspond to a value slightly above (e.g., 10% above) a corresponding value for a therapy interruption, which can correspond to a value at which the current generator circuit of the IPG cannot supply adequate current and/or therapy to the patient. The threshold break can be used as a break point to adjust $V_S$ before actual therapy is interrupted (e.g., if $V_S$ fell below $V_{MIN}$). Based on the first threshold break, the system determines an increased $V_S$ value and/or adjusted operating parameters to be used in the second iteration (2). The system may also store the $V_S$ value at which the first threshold break occurred, as this value can be used to help determine $V_S$ and operating parameter values for subsequent iterations (e.g., the third iteration). Following the first iteration (1), the second iteration (2) begins by adjusting $V_S$ to the most recently sent (e.g., inputted) $V_S$ value, resulting in a $V_S$ step 512. The system then decreases $V_S$ along path 514 according to the most recently sent operating parameters, which then results in a second threshold break. The $V_S$ value associated with step 512 is closer to $V_{MIN}$, compared to the previous starting $V_S$ value for the first iteration (1), and the slope of the path 514 more closely mirrors the $V_{MIN}$ profile, compared to the slope of the previous $V_S$ path 510. Following the second threshold break, the system can consider and/or store the $V_S$ values for the first and second threshold breaks, and can follow a similar set of operations for the third iteration (3).

As shown by the first portion 502 of the simulation, the system allows $V_S$ to continually approach and track $V_{MIN}$ with each subsequent iteration. For example, the $V_S$ step value for each subsequent iteration can be closer to $V_{MIN}$ than the step value for the preceding iteration. Additionally, the operating parameters for each subsequent iteration can result in a slope that more closely reflects the slope of $V_{MIN}$, compared to the slope of the preceding iteration. As such, the system is iteratively tuned to decrease power loss from the system (e.g., via dissipated heat) with each additional iteration that is performed.

In part, this is because each additional iteration and threshold break provide further data about the profile of $V_{MIN}$ to the system. For example, the $V_S$ step value and operating parameters inputted and used for the fourth iteration (4) can be based on the first, second, and/or third threshold breaks, as opposed to the $V_S$ step value and operating parameters used for the second iteration (2), which may only be based on the first threshold break. As such, each additional iteration allows the system to develop a more accurate profile of $V_{MIN}$ and its increasing, decreasing, or steady characteristics or rate of change.

The second portion 503 of the plot 500 corresponds to an increasing $V_{MIN}$ profile. Here, the third threshold break following the third iteration (3) indicates to the system that $V_{MIN}$ is slightly increasing, at least because $V_{MIN}$ at the third threshold break is higher than $V_{MIN}$ at the second threshold break. As such, the system can determine that the change of $V_{MIN}$ from the second to third threshold breaks is slightly greater than the change of $V_{MIN}$ from the first to second threshold breaks. Based on the previous first, second and/or third threshold breaks, the system can provide adjusted values for $V_S$ and operating parameters to be used in the fourth iteration (4). The $V_S$ step 530 for the fourth iteration (4) may be similar to the $V_S$ step 516 for the third iteration (3) because the system has enough data points now to predict that the $V_{MIN}$ is increasing. For similar reasons, the operating parameters used for the fourth iteration (4) result in a slope that is more positive (i.e., only slightly negative or close to zero).

The fourth threshold break corresponds to a $V_{MIN}$ higher than the $V_{MIN}$ of the third threshold break, which indicates to the system that $V_{MIN}$ is still increasing, but at a faster rate than previously expected. Accordingly, values for $V_S$ and operating parameters are adjusted for the fifth iteration (5) and may include a smaller $V_S$ step 534 and a positive slope 436 that attempts to more closely mirror the change or rate of change of $V_{MIN}$. The fifth threshold break following the fifth iteration (5) can indicate that $V_{MIN}$ has attained a steady increasing profile similar to the $V_{MIN}$ profile determined at the fourth threshold break. Therefore, the sixth iteration (6) may include an even smaller $V_S$ step 538, compared to $V_S$ step 534, and a slope 540 that again is more similar to the $V_{MIN}$ profile, compared to slope 536. As a general matter, the step size (e.g., for steps 530, 534, 538) and the slope (e.g., slopes 532, 536, 540) reflect how well the system understands the current profile of $V_{MIN}$ at that time. If the $V_{MIN}$ profile is experiencing a change (e.g., from a steady profile to an increasing profile), then the step size may be relatively large (e.g., to ensure $V_S$ is above $V_{MIN}$), and the slope may be relatively steep (e.g., a more negative slope). This large step size and steep slope can help gather an additional data point corresponding to the $V_{MIN}$ profile relatively quickly. Alternatively, if the $V_{MIN}$ profile is not experiencing a change or rate of change in profile (e.g., $V_{MIN}$ is increasing at a steady rate), then the step size may be relatively small because the system can better predict the current profile of $V_{MIN}$, and the slope may be less steep to more closely reflect the current profile of $V_{MIN}$.

The sixth iteration (6) also includes a portion 542 wherein the slope of $V_S$ changes from positive to negative. This change may be initiated if and when a threshold break has not occurred within a given time. For example, in some embodiments, in addition to determining new values for $V_S$ and operating parameters for a subsequent iteration, the system may also determine an elapsed time limit before which the next threshold break should occur. This elapsed time limit may differ for each iteration. As an example, if the system does not experience a threshold break within an elapsed time limit of, e.g., 35 milliseconds for a given iteration, $V_S$ may be automatically decreased, or decreased at a faster rate, to cause a threshold interruption. The elapsed time limit can help prevent $V_S$ from veering too far away from $V_{MIN}$, and thereby limit unnecessary power loss from the system. The elapsed time limit can be a preset value manually inputted by an operator or physician, or can be a determined value that is dynamically adjusted depending on $V_{MIN}$ and its relationship to $V_S$ at that time.

The third portion 504 of the plot 500 corresponds to a decreasing $V_{MIN}$ profile. As shown by the seventh iteration (7), the $V_S$ step 550 may be larger than the previous $V_S$ step 538 because the sixth threshold break occurred after the elapsed time limit was initiated, thereby indicating that the $V_{MIN}$ profile may no longer be increasing at the previously expected rate. As such, the inputted $V_S$ for the seventh iteration (7) may be higher than the previous iteration (6) to ensure $V_S$ remains above $V_{MIN}$ and adequate therapy continues to be provided to the patient (e.g., a therapy interruption is avoided). For similar reasons, the operating parameters inputted for the seventh iteration (7) may result in a negative slope 552 to ensure a threshold break occurs relatively quickly. Following the threshold break after the seventh iteration (7), the system determines that $V_{MIN}$ is decreasing. In this case, because the previous iteration had a substantially different profile (i.e., an increasing profile), the system may not consider one or more of the previous threshold breaks.

The subsequent eighth iteration (8) and ninth iteration (9) can exhibit features similar to those previously described with reference to the first portion 502 and second portion 503. For example, values for the $V_S$ and operating parameters for the eighth iteration (8) can be based on the previous threshold breaks, and can result in a $V_S$ step 554 which is smaller than the $V_S$ step 550, and a slope 556 that more closely mirrors the $V_{MIN}$ profile, compared to slope 552. Using the same methodology, the $V_S$ step 558 for the ninth iteration (9) is smaller than $V_S$ step 554 for the eighth iteration (8), and the slope 560 more closely mirrors the $V_{MIN}$ profile, compared to the slope 556. Accordingly, each subsequent iteration can bring $V_S$ closer to $V_{MIN}$, thereby decreasing power loss as therapy continues to be delivered.

From the foregoing, it will be appreciated that specific embodiments of the presently disclosed technology have been described herein for purposes of illustration, but that various modifications may be made without deviating from the disclosed technology. For example, some embodiments were described above in the context of adjusting an electrical signal based on voltage. In some embodiments, other methodologies may be used, such as adjusting the electrical signal based on current, impedance, frequency, amplitude or other variable parameters of the electrical signal. As such, other factors for delivering and adjusting the electrical signal parameter can also change depending on the parameter(s) used. For example, when adjusting the electrical signal based on impedance, the threshold break may occur when the impedance of the electrical signal rises to or above a threshold impedance, instead of falling to or below a threshold voltage, as is the case for adjusting the electrical signal based on voltage.

As another example, some embodiments were described above in the context of particular therapy signals that produce pain relief without generating paresthesia. In some embodiments, other methodologies may be used to provide pain therapy to the patient, and in some instances, such methodologies may provide paresthesia-free pain relief. In some embodiments, techniques generally similar to those described above may be applied to therapies that are directed to tissues other than the spinal cord. Representative tissues can include peripheral nerve tissue and/or brain tissue.

In some embodiments, similar or identical techniques for handling charging and/or discharging processes and parameters may be used in the context of therapy parameters that generate paresthesia. Some embodiments were described above in the context of spinal cord stimulators, and in some embodiments, generally similar or identical charge parameter selection techniques can be used for implantable devices that perform functions other than spinal cord stimulation. In some embodiments discussed above, retrieving, processing and/or other data functions are performed at the IPG. In some embodiments, at least some of the foregoing processes can be carried out by another component of the overall system, for example, a non-implantable component. In particular, certain processes can be carried out by a charger, based on data provided by the IPG at the time of charging.

Many of the foregoing processes include determining values, parameters, ranges and/or other quantities. As used herein, "determining" can include calculating, extrapolating, interpolating, applying table look up functions, estimating, and/or other suitable methods. As used herein, "generally" or "approximately," when preceding a value, should be interpreted to mean plus or minus 10% of the value, unless otherwise indicated.

Certain aspects of the technology described in the context of some embodiments may be combined or eliminated in some embodiments. For example, in some embodiments, the foregoing techniques can include using patient-specific therapy parameters, or battery-specific battery parameters, or a combination of both. In some embodiments, certain steps of an overall process can be re-ordered or eliminated.

While advantages associated with some embodiments of the disclosed technology have been described in the context of those embodiments, other embodiments may also exhibit such advantages, and not all embodiments need necessarily exhibit such advantages to fall within the scope of the present technology. The examples presented in the following section provide further embodiments of the present technology.

To the extent that any of the foregoing patents, published applications, and/or other materials incorporated herein by reference conflict with present disclosure, the present disclosure controls.

The subject technology is illustrated, for example, according to various aspects described below. Various examples of aspects of the subject technology are described as numbered examples (1, 2, 3, etc.) for convenience. These are provided as examples and do not limit the subject technology. It is noted that any of the dependent examples may be combined in any combination, and placed into a respective independent example, (e.g., examples 1, 6 or 17). The other examples can be presented in a similar manner.

EXAMPLES

1. A method for delivering electrical therapy to a patient in a closed loop manner, the method comprising:
   delivering, via an implantable pulse generator, a variable electrical signal having a parameter with a first parameter value;
   adjusting the parameter of the electrical signal from the first parameter value;
   receiving an indication of a first threshold break, corresponding to the parameter exceeding or falling below a first threshold value of the parameter; and in response to the received indication—
   increasing the parameter by a step size to a second parameter value; and adjusting the parameter along a determined slope until a second threshold break occurs.

2. The method of example 1 wherein the step size is a first step size, and wherein the second threshold break occurs at a second threshold value different than the first threshold value, the method further comprising:
based at least in part on the first and second threshold values, increasing the parameter by a second step size different than the first step size.

3. The method of example 2 wherein increasing the parameter by the second step size is based at least in part on a length of time between the first and second threshold breaks, and wherein the second step size is less than the first step size.

4. The method of example 2 wherein the determined slope is a first determined slope, the method further comprising:
based on at least one of (a) the first and second threshold values or (b) a length of time between the first and second threshold breaks, adjusting the parameter along a second determined slope, different than the first determined slope, until a third threshold break occurs.

5. The method of example 1 wherein:
the parameter is a voltage,
the first parameter value is a first voltage value, and
delivering the electrical signal includes delivering the electrical signal from a voltage regulator to a current generating source.

6. A method for adjusting an electrical signal associated with delivering therapy to a patient, the method comprising:
delivering, via an implantable pulse generator, an electrical signal having a parameter with a first parameter value;
adjusting the parameter of the electrical signal from the first parameter value until a threshold break occurs at a second parameter value that is equal to or less than a threshold value; and
in response to the threshold break, increasing the second parameter value to a third parameter value.

7. The method of example 6 wherein the parameter corresponds to a voltage, and wherein adjusting the parameter includes decreasing the voltage from the first parameter value to the second parameter value based at least in part on a length of time between the threshold break and a previous threshold break.

8. The method of example 6 wherein the parameter corresponds to a voltage, and wherein adjusting the parameter includes increasing the voltage from the first parameter value to the second parameter value based at least in part on a length of time between the threshold break and a previous threshold break.

9. The method of example 6, further comprising determining a minimum parameter value below which therapy is not delivered to the patient, wherein the threshold value is above the minimum parameter value.

10. The method of example 6, further comprising, after increasing the parameter of the electrical signal to the third parameter value, adjusting the parameter of the electrical signal based at least in part on a length of time between the threshold break and a previous threshold break.

11. The method of example 6 wherein the third parameter value is less than the first parameter value and greater than the second parameter value.

12. The method of example 6 wherein the parameter is a voltage, and wherein delivering the electrical signal includes delivering the electrical signal from a voltage regulator to a current generating source, the method further comprising:
converting the voltage provided by the voltage regulator to a requested current that is delivered to the patient.

13. The method of example 6 wherein the threshold break is a first threshold break occurring at a first point in time, the method further comprising:
delivering, via the implantable pulse generator, the electrical signal having the third parameter value;
adjusting the parameter of the electrical signal from the third parameter value until a second threshold break occurs at a fourth parameter value; and
in response to the second threshold break, increasing the parameter of the electrical signal to a fifth parameter value.

14. The method of example 13 wherein increasing the parameter of the electrical signal to a fifth parameter value is based at least in part on the first threshold break.

15. The method of example 13 wherein adjusting the parameter from the third parameter value is based at least in part on a length of time between the first and second threshold breaks.

16. The method of example 13 wherein:
delivering the electrical signal and adjusting the parameter of the electrical signal from the first parameter value comprise a first iteration of a closed-feedback loop,
increasing the parameter of the electrical signal to the third parameter value, delivering the electrical signal at the third parameter value, and adjusting the electrical signal from the third parameter value, comprise a second iteration of a feedback loop, subsequent to the first iteration, and
increasing the parameter to the fifth parameter value comprises a third iteration of the feedback loop, subsequent to the second iteration.

17. An implantable device configured to deliver therapy to a patient, the device comprising:
a battery;
a voltage regulator coupled to the battery and configured to produce a supply voltage;
a current-generating circuit configured to supply a current to the device based at least in part on the supply voltage; and
a computer-readable medium having instructions that, when executed,
cause the device to—
deliver the supply voltage, having a first value, from the voltage regulator to the current-generating circuit;
adjust the supply voltage from the first value until a threshold break occurs, the threshold break corresponding to a second value of the supply voltage at or below a threshold value; and
in response to the threshold break, increase the supply voltage from the second value to a third value.

18. The device of example 17 wherein:
the current supplied to the device is a requested current from the device,
the threshold value is above a minimum voltage value below which the current generating source is prevented from supplying the requested current to the device, and
the computer-readable medium is configured to control a difference between values of the minimum voltage and the supply voltage.

19. The device of example 17 wherein:
the threshold break is a first threshold break occurring at a first period in time,
the operations of delivering the variable supply voltage and adjusting the supply voltage comprise a first iteration, and the instructions further cause the device to:
deliver the supply voltage at the third value, from the voltage regulator to the current-generating circuit;
adjust the supply voltage from the third value until a second threshold break occurs, the second threshold break corresponding to a fourth value of the supply voltage at or below a threshold value at a second period in time after the first period in time; and
based at least in part on the second threshold break, increase the supply voltage from the fourth value to a fifth value.

20. The method of example 19 wherein:
adjusting the supply voltage from the third value includes adjusting the supply voltage from the third value based at least in part on a length of time between the first and second threshold breaks; and
increasing the supply voltage to the fifth value is further based at least in part on the second value.

The invention claimed is:

1. A method for adjusting an electrical signal associated with delivering therapy to a patient, the method comprising:
delivering, via an implantable pulse generator, an electrical signal having a parameter with a first parameter value;
determining a minimum parameter value below which therapy is not delivered to the patient;
adjusting the parameter of the electrical signal from the first parameter value until a threshold break occurs at a second parameter value that is equal to or less than a threshold value, wherein the threshold value is above the minimum parameter value; and
in response to the threshold break, increasing the second parameter value to a third parameter value.

2. The method of claim 1 wherein the parameter corresponds to a voltage, and wherein adjusting the parameter includes decreasing the voltage from the first parameter value to the second parameter value based at least in part on a length of time between the threshold break and a previous threshold break.

3. The method of claim 1 wherein the parameter corresponds to a voltage, and wherein adjusting the parameter includes increasing the voltage from the first parameter value to the second parameter value based at least in part on a length of time between the threshold break and a previous threshold break.

4. The method of claim 1, further comprising, after increasing the parameter of the electrical signal to the third parameter value, adjusting the parameter of the electrical signal based at least in part on a length of time between the threshold break and a previous threshold break.

5. The method of claim 1 wherein the third parameter value is less than the first parameter value and greater than the second parameter value.

6. The method of claim 1 wherein the parameter is a voltage, and wherein delivering the electrical signal includes delivering the electrical signal from a voltage regulator to a current generating source, the method further comprising:
converting the voltage provided by the voltage regulator to a requested current that is delivered to the patient.

7. The method of claim 1 wherein the threshold break is a first threshold break occurring at a first point in time, the method further comprising:
delivering, via the implantable pulse generator, the electrical signal having the third parameter value;
adjusting the parameter of the electrical signal from the third parameter value until a second threshold break occurs at a fourth parameter value; and
in response to the second threshold break, increasing the parameter of the electrical signal to a fifth parameter value.

8. The method of claim 7 wherein increasing the parameter of the electrical signal to a fifth parameter value is based at least in part on the first threshold break.

9. The method of claim 7 wherein adjusting the parameter from the third parameter value is based at least in part on a length of time between the first and second threshold breaks.

10. The method of claim 7 wherein:
delivering the electrical signal and adjusting the parameter of the electrical signal from the first parameter value comprise a first iteration of a closed-feedback loop,
increasing the parameter of the electrical signal to the third parameter value, delivering the electrical signal at the third parameter value, and adjusting the electrical signal from the third parameter value, comprise a second iteration of a feedback loop, subsequent to the first iteration, and
increasing the parameter to the fifth parameter value comprises a third iteration of the feedback loop, subsequent to the second iteration.

11. An implantable device configured to deliver therapy to a patient, the device comprising:
a battery;
a voltage regulator coupled to the battery and configured to produce a supply voltage;
a current-generating circuit configured to supply a current to the device based at least in part on the supply voltage; and
a computer-readable medium having instructions that, when executed, cause the device to—
deliver the supply voltage, having a first value, from the voltage regulator to the current-generating circuit;
adjust the supply voltage from the first value until a threshold break occurs, the threshold break corresponding to a second value of the supply voltage at or below a threshold value, wherein the threshold value is above a minimum voltage value below which the current-generating circuit is prevented from supplying the requested current to the device; and
in response to the threshold break, increase the supply voltage from the second value to a third value.

12. The device of claim 11 wherein:
the current supplied to the device is a requested current from the device, and
the computer-readable medium is configured to control a difference between values of the minimum voltage and the supply voltage.

13. The device of claim 11 wherein:
the threshold break is a first threshold break occurring at a first period in time,
the operations of delivering the variable supply voltage and adjusting the supply voltage comprise a first iteration, and
the instructions further cause the device to:
deliver the supply voltage at the third value, from the voltage regulator to the current-generating circuit;
adjust the supply voltage from the third value until a second threshold break occurs, the second threshold break corresponding to a fourth value of the supply voltage at or below a threshold value at a second period in time after the first period in time; and based at least in part on the second threshold break, increase the supply voltage from the fourth value to a fifth value.

14. The device of claim 13 wherein:
adjusting the supply voltage from the third value includes adjusting the supply voltage from the third value based at least in part on a length of time between the first and second threshold breaks; and
increasing the supply voltage to the fifth value is further based at least in part on the second value.

15. The method of claim 1 wherein adjusting the parameter includes automatically adjusting the parameter, and wherein increasing the second parameter value includes automatically increasing the second parameter value.

16. The device of claim 11 wherein the operation of adjusting the supply voltage includes automatically adjusting the supply voltage, and wherein the operation of increasing the supply voltage includes automatically increasing the supply voltage.

17. The method of claim 1 wherein the second parameter value is equal to or greater than the minimum parameter value.

18. The device of claim 11 wherein the second value of the supply voltage is equal to or greater than the minimum voltage value.

19. A method for adjusting an electrical signal associated with delivering therapy to a patient, the method comprising:
delivering, via an implantable pulse generator, an electrical signal having a parameter with a first parameter value;
adjusting the parameter of the electrical signal from the first parameter value until a threshold break occurs at a second parameter value that is equal to or less than a threshold value, wherein the threshold value is above a minimum parameter value below which therapy is not delivered to the patient; and
in response to the threshold break, increasing the second parameter value to a third parameter value.

* * * * *